(12) United States Patent
Kidwell, Jr. et al.

(10) Patent No.: US 10,109,784 B2
(45) Date of Patent: Oct. 23, 2018

(54) SENSOR DEVICE

(71) Applicant: QUALCOMM Incorporated, San Diego, CA (US)

(72) Inventors: Donald William Kidwell, Jr., Los Gatos, CA (US); Ravindra Shenoy, Dublin, CA (US); Jon Lasiter, Stockton, CA (US)

(73) Assignee: QUALCOMM Incorporated, San Diego, CA (US)

( * ) Notice: Subject to any disclaimer, the term of this patent is extended or adjusted under 35 U.S.C. 154(b) by 276 days.

(21) Appl. No.: 15/262,721

(22) Filed: Sep. 12, 2016

(65) Prior Publication Data

US 2017/0256699 A1 Sep. 7, 2017

Related U.S. Application Data

(60) Provisional application No. 62/302,085, filed on Mar. 1, 2016.

(51) Int. Cl.
*H01L 41/04* (2006.01)
*B06B 1/06* (2006.01)
(Continued)

(52) U.S. Cl.
CPC ........ *H01L 41/1132* (2013.01); *B06B 1/0622* (2013.01); *H01L 41/042* (2013.01);
(Continued)

(58) Field of Classification Search
CPC .............. H01L 41/1132; H01L 41/042; H01L 41/0472; H01L 41/083; H01L 41/187; H01L 41/23; H01L 41/277; B06B 1/0622
(Continued)

(56) References Cited

U.S. PATENT DOCUMENTS 5,744,898 A 4/1998 Smith et al.
8,596,140 B2 12/2013 Skallebaek et al.
(Continued)

FOREIGN PATENT DOCUMENTS

WO WO-2010082993 A2 11/2007
WO WO-2016007250 A1 1/2016

OTHER PUBLICATIONS

International Search Report and Written Opinion—PCT/US2017/014555—ISA/EPO—dated Aug. 14, 2017.

*Primary Examiner* — Thomas Dougherty
(74) *Attorney, Agent, or Firm* — Silicon Valley Patent Group LLP

(57) ABSTRACT

Embodiments of a sensor device and methods for manufacturing the same are disclosed. In one embodiment, a sensor device comprises a piezoelectric micromechanical ultrasonic transducer (PMUT) array configured to transmit and receive ultrasonic signals, where the PMUT array comprises a plurality of PMUTs and the PMUT array is flexible, one or more integrated circuits configured to process the ultrasonic signals, a battery configured to provide power to the PMUT array and the one or more integrated circuits, a coupling material configured to hold the PMUT array, the one or more integrated circuits, and the battery, and a capsule configured to seal the PMUT array, the one or more integrated circuits, the battery and the coupling material within the capsule.

30 Claims, 27 Drawing Sheets

(51) Int. Cl.
      *H01L 41/113*   (2006.01)
      *H01L 41/083*   (2006.01)
      *H01L 41/187*   (2006.01)
      *H01L 41/047*   (2006.01)
      *H01L 41/277*   (2013.01)
      *H01L 41/23*    (2013.01)
(52) U.S. Cl.
      CPC ........ *H01L 41/0472* (2013.01); *H01L 41/083* (2013.01); *H01L 41/187* (2013.01); *H01L 41/23* (2013.01); *H01L 41/277* (2013.01)
(58) Field of Classification Search
      USPC .................... 310/322, 334, 340; 29/25.35
      See application file for complete search history.

(56)  References Cited

U.S. PATENT DOCUMENTS

| | | |
|---|---|---|
| 8,647,328 B2 | 2/2014 | Porat et al. |
| 2007/0013269 A1* | 1/2007 | Huang .................. B06B 1/0292 |
| | | 310/334 |
| 2007/0264732 A1 | 11/2007 | Chen |
| 2011/0130658 A1 | 6/2011 | Iddan |
| 2014/0276079 A1 | 9/2014 | Yamagata et al. |
| 2016/0256133 A1* | 9/2016 | Dekker ............... H01L 23/5386 |

\* cited by examiner

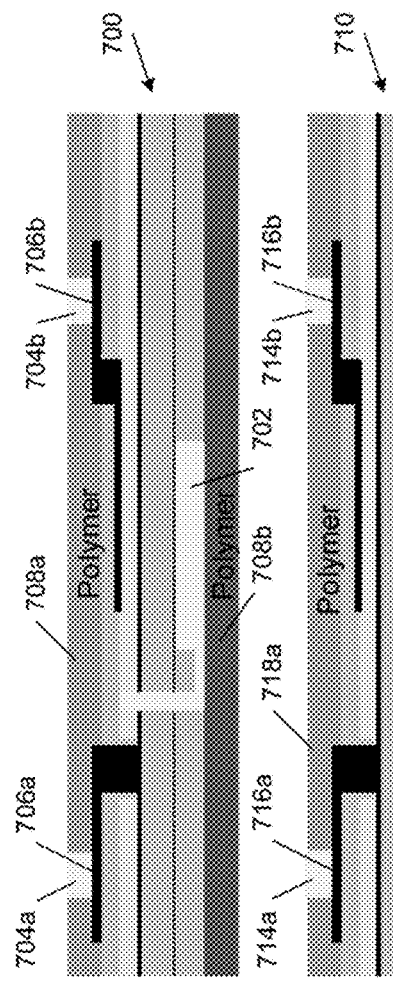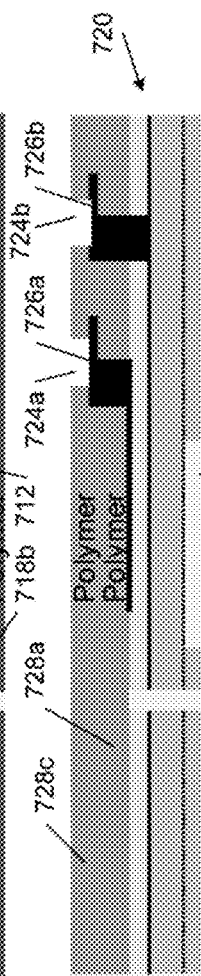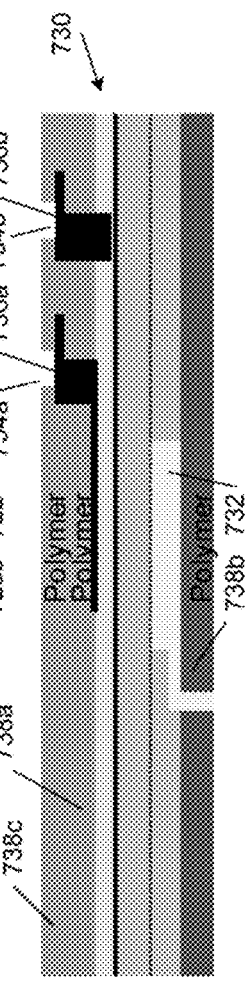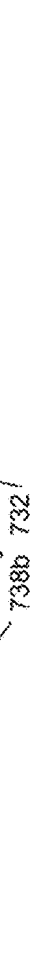

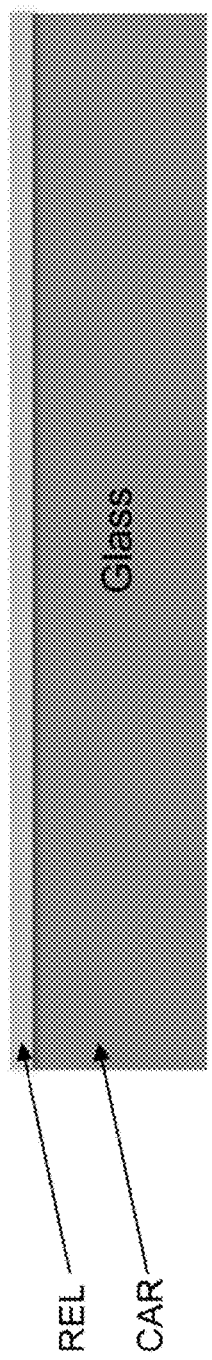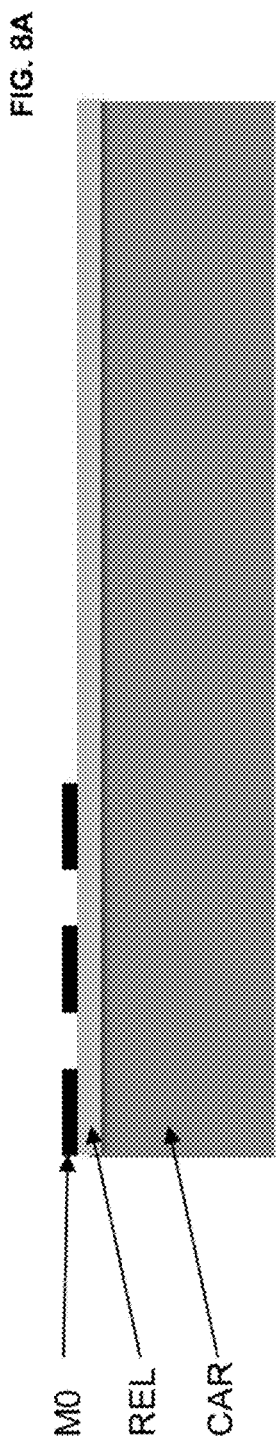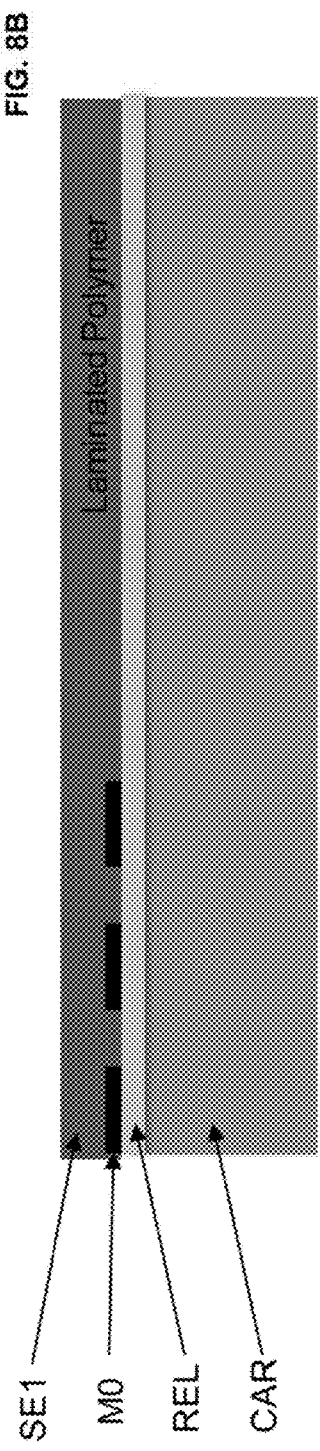

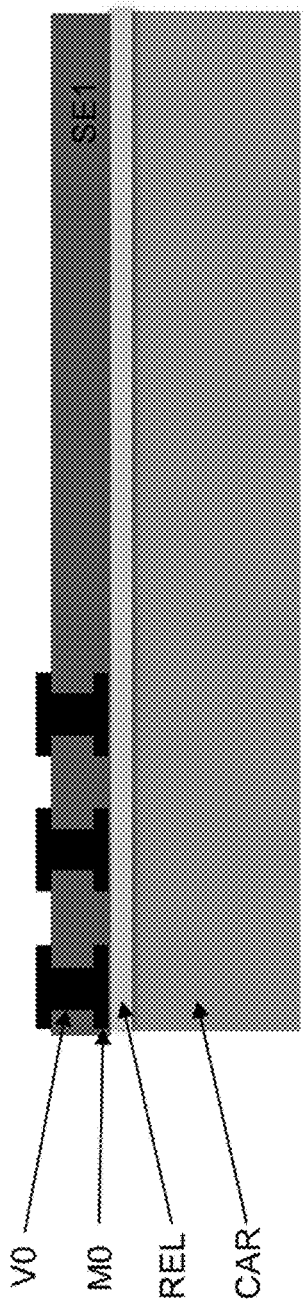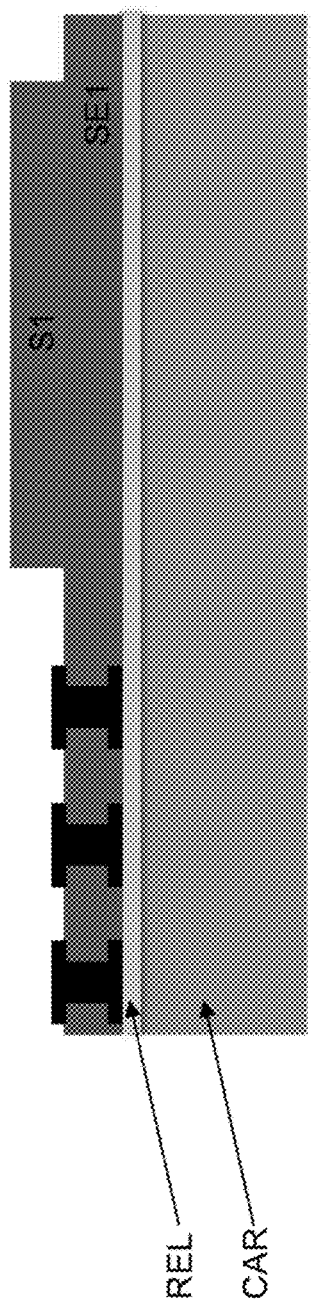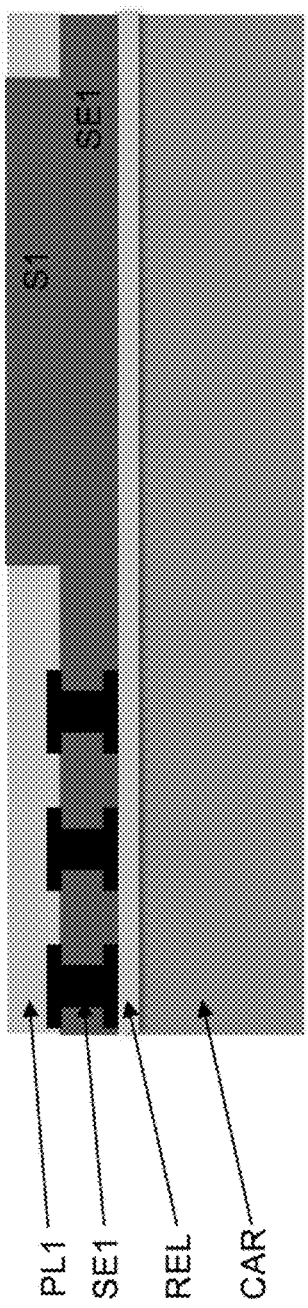

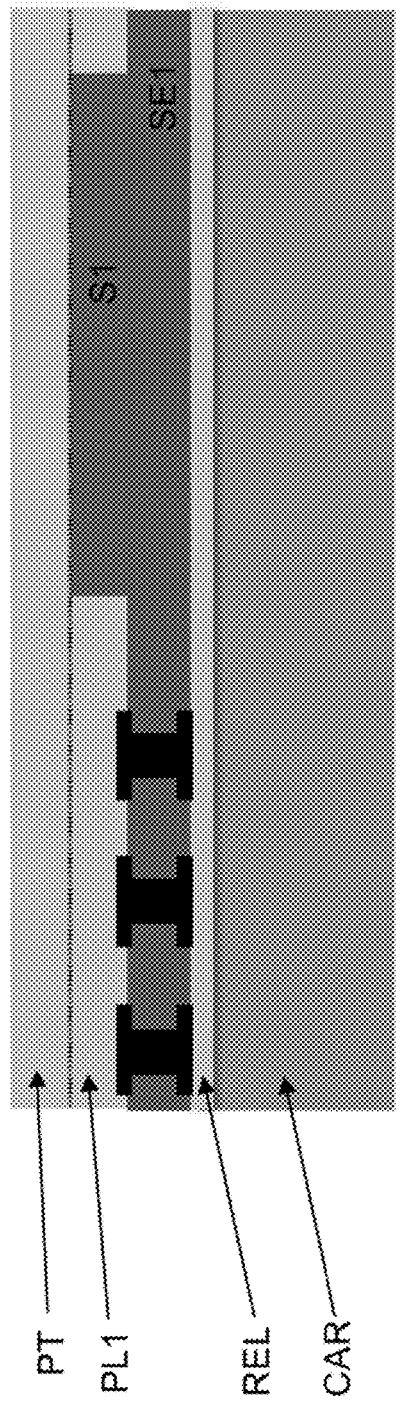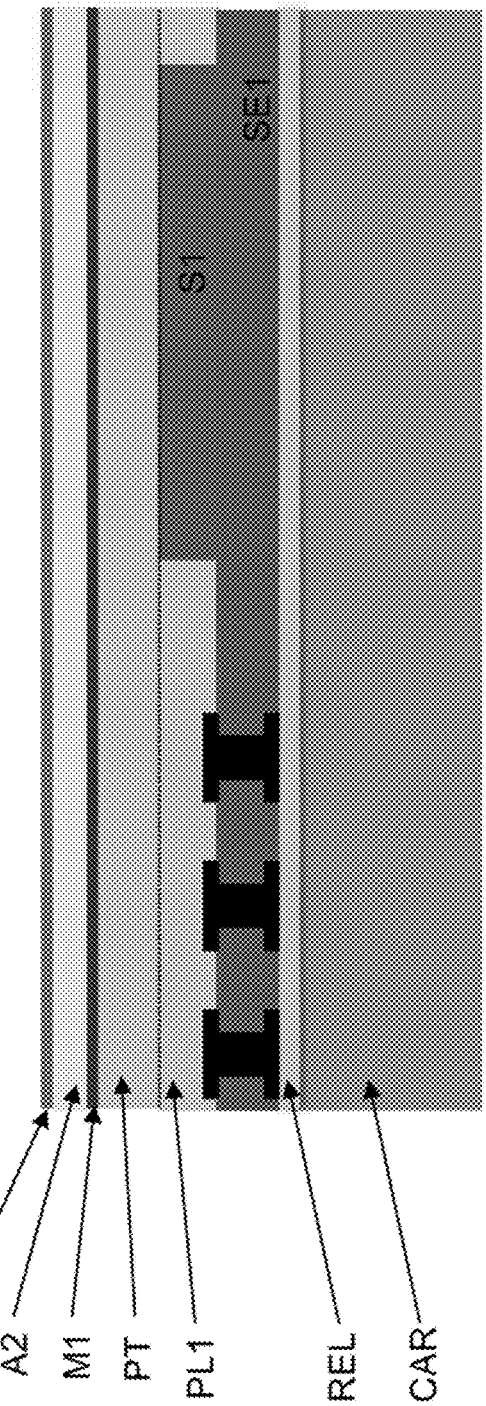
FIG. 8G
FIG. 8H

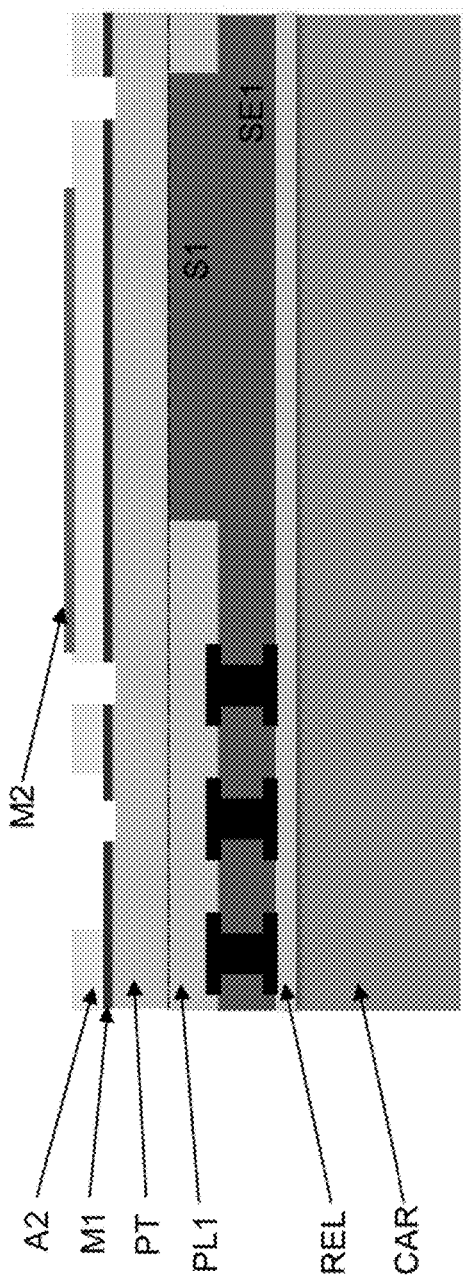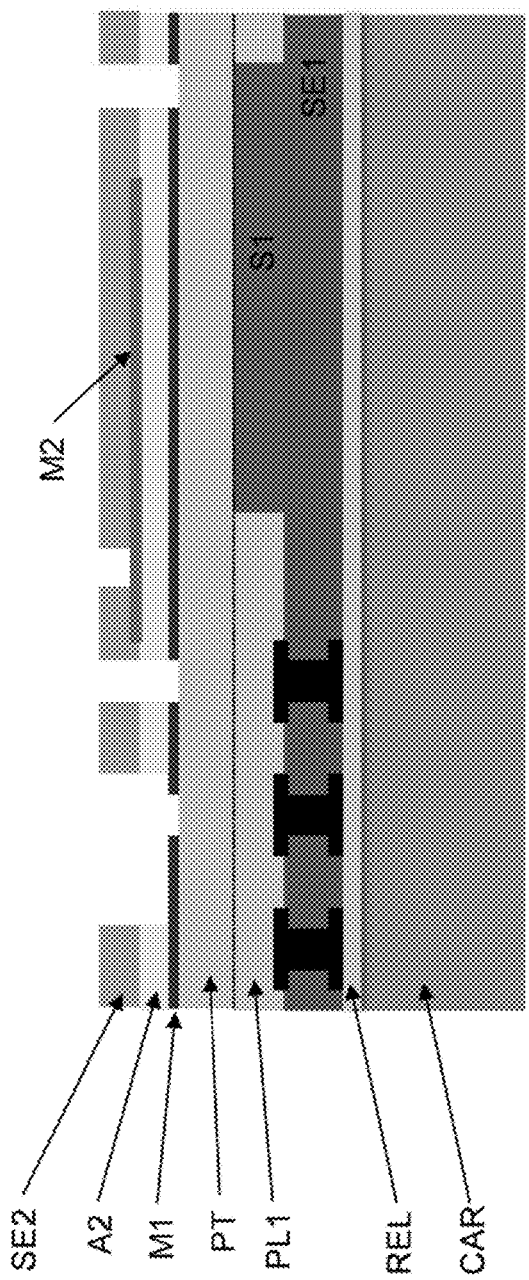

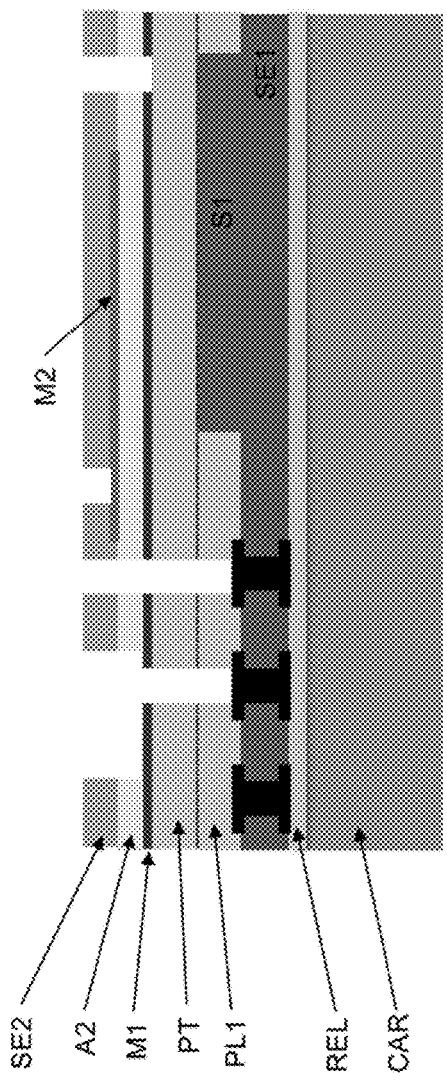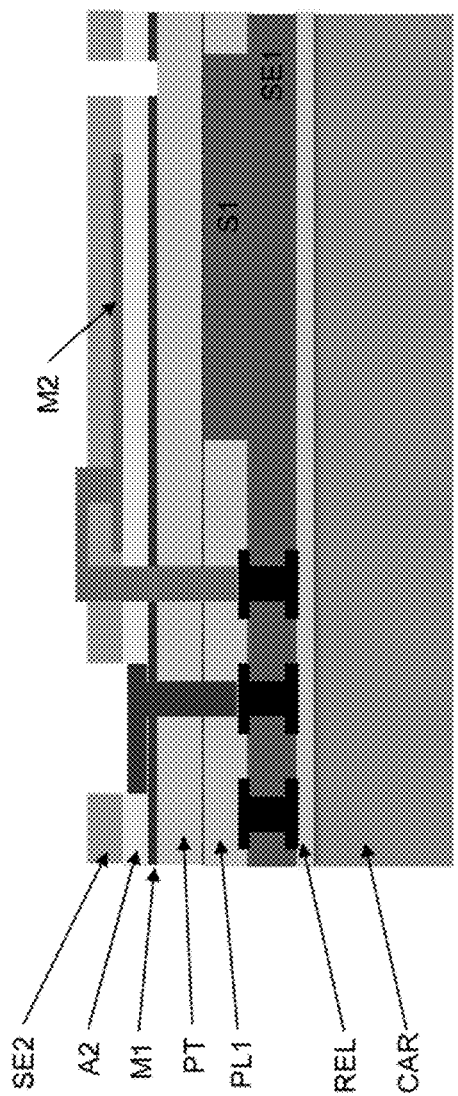

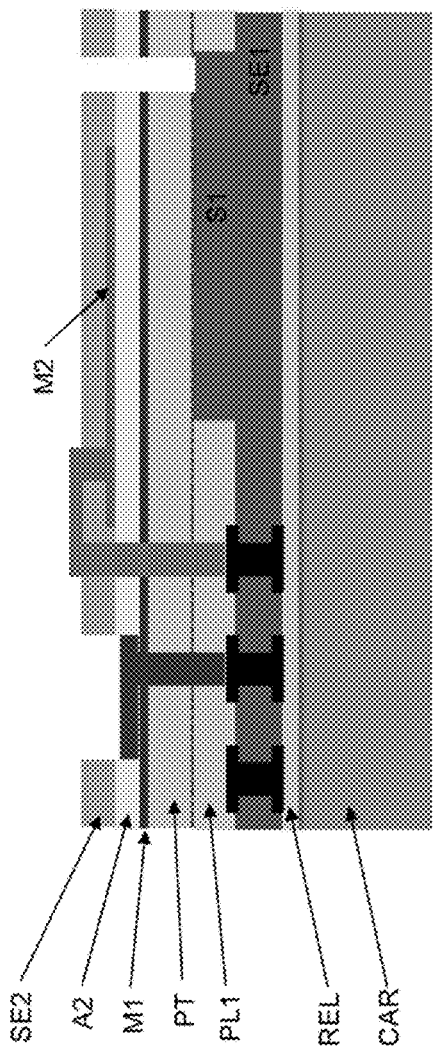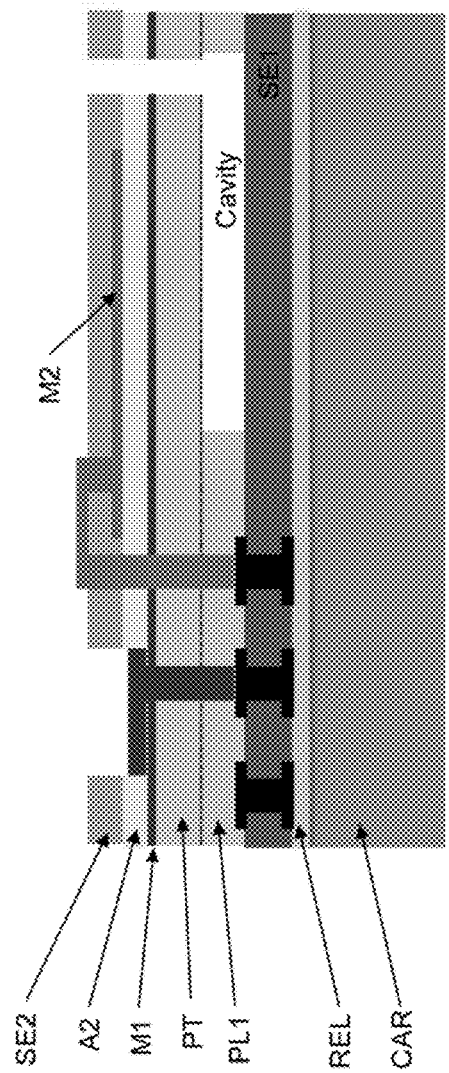

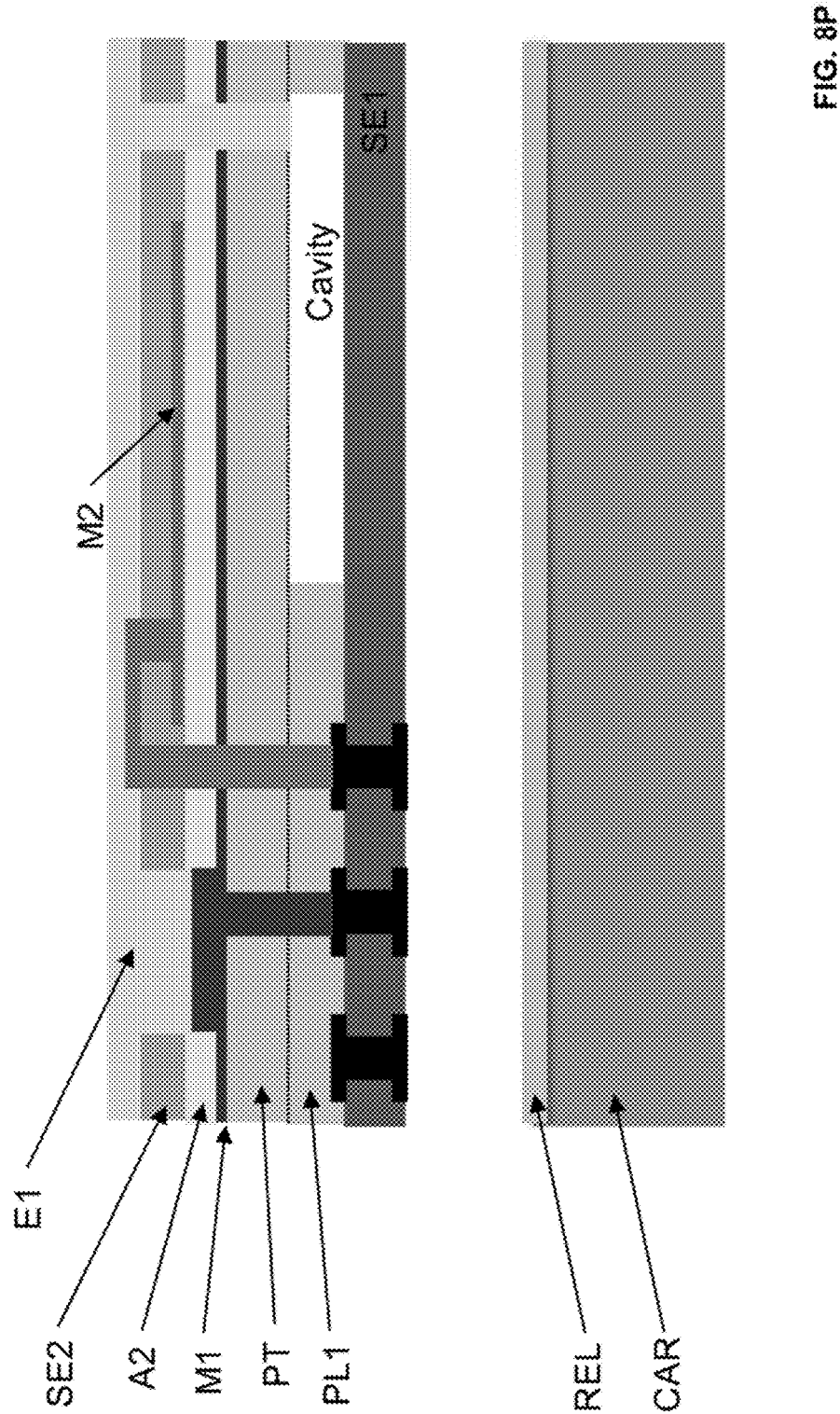

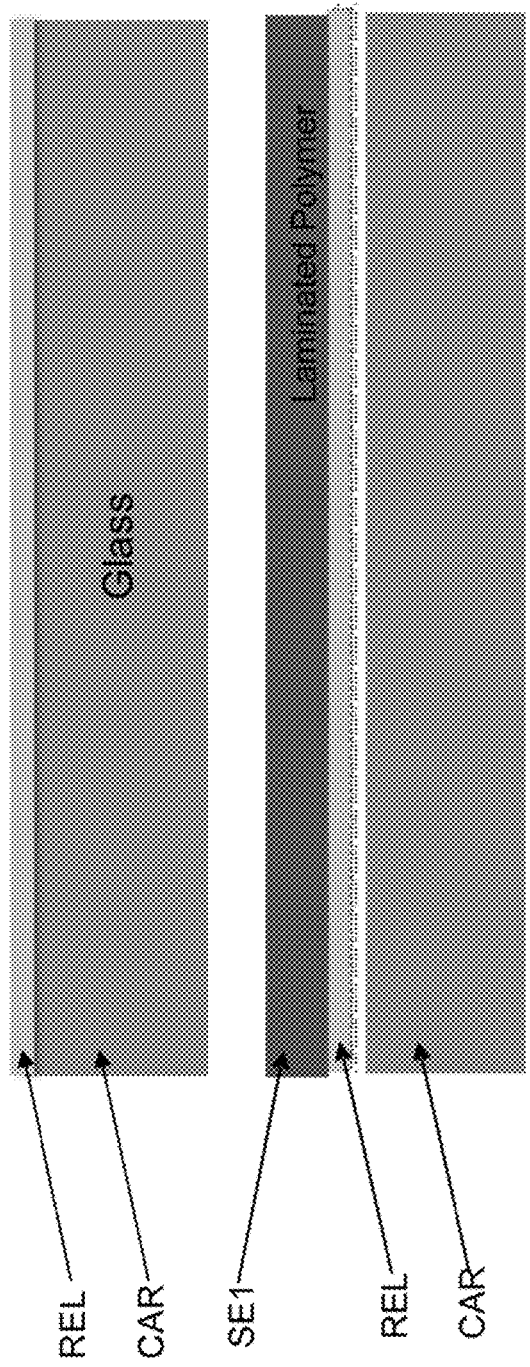
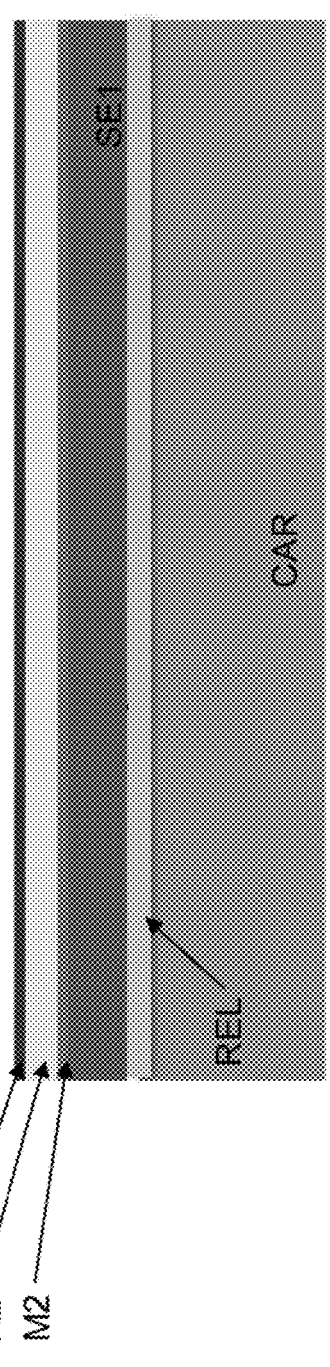
FIG. 9A
FIG. 9B
FIG. 9C

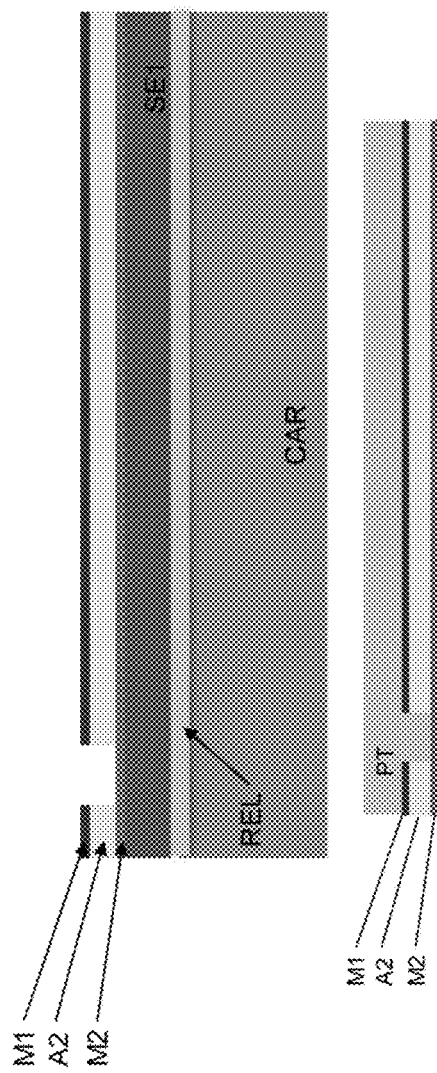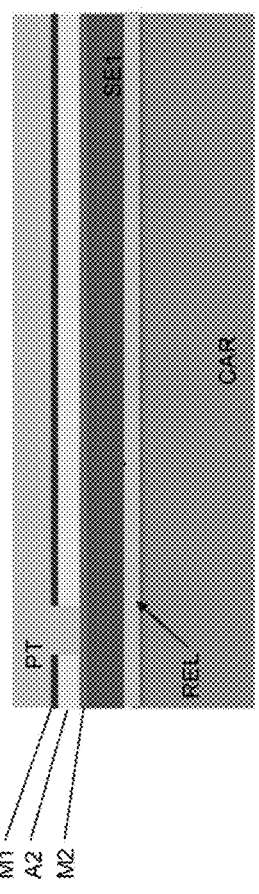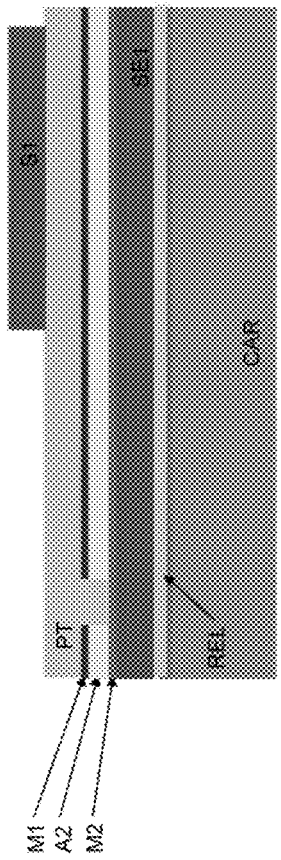

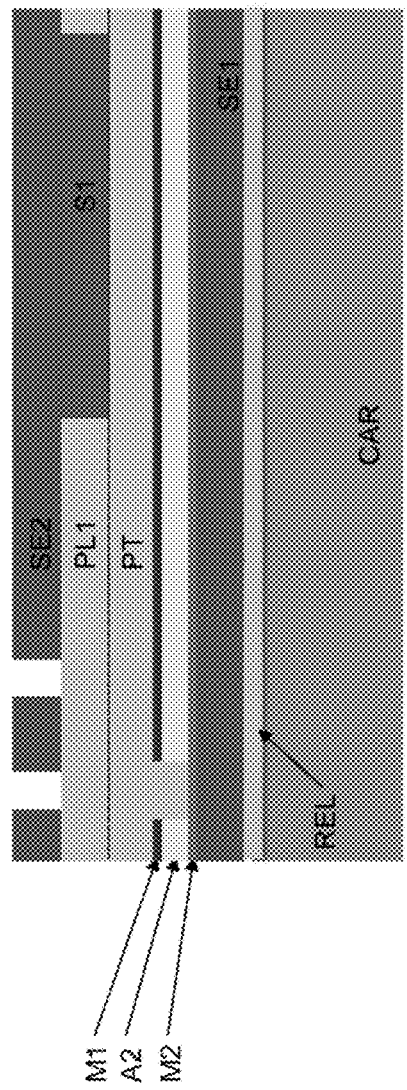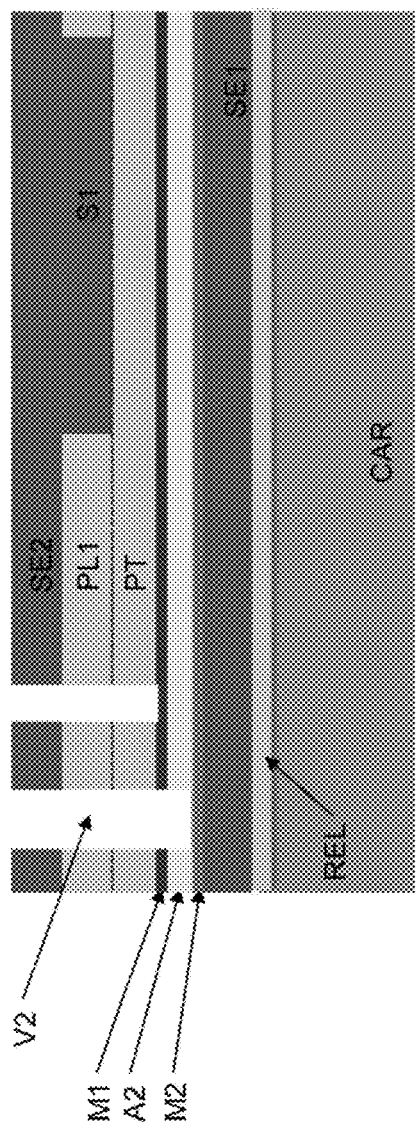

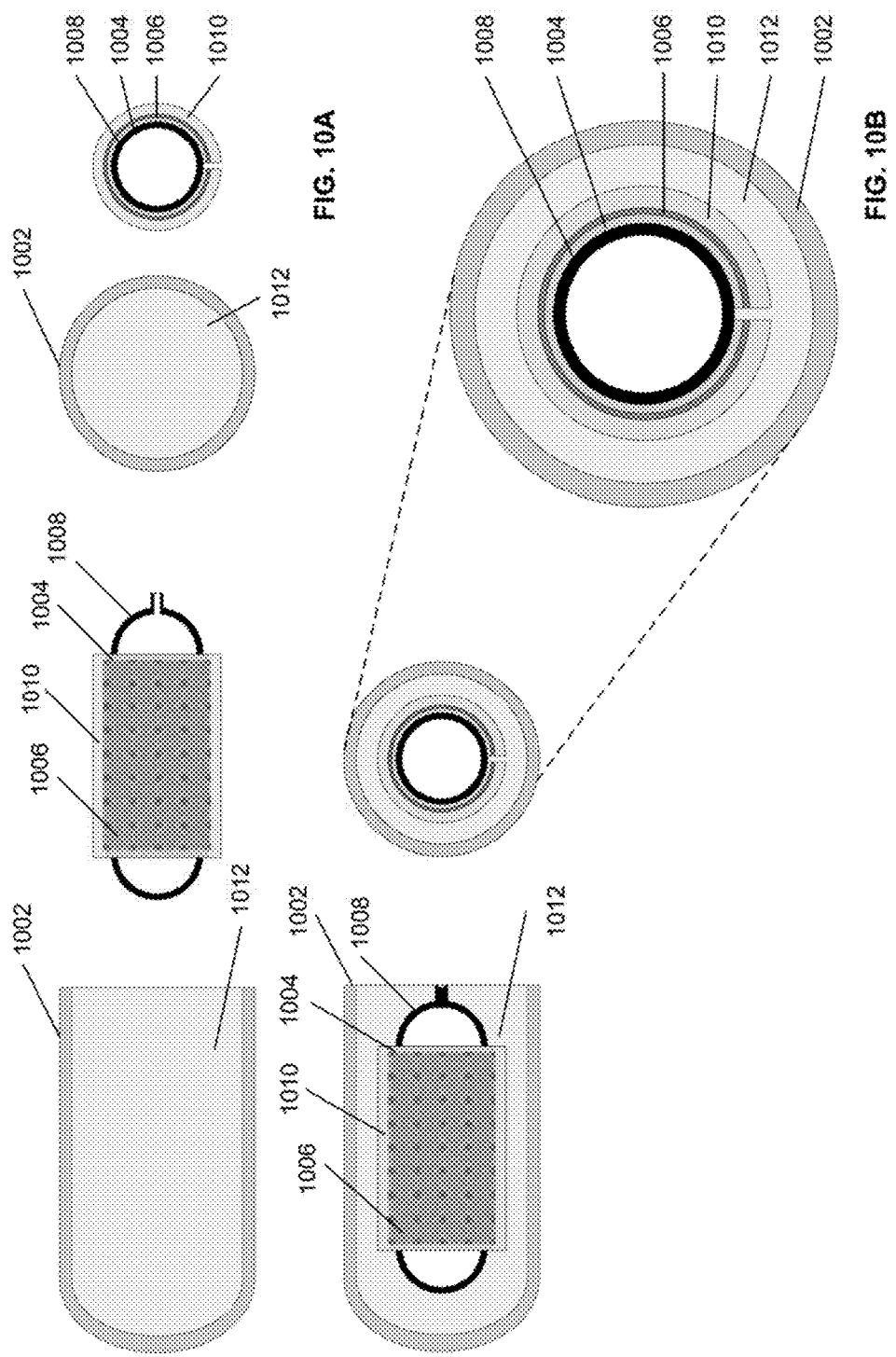

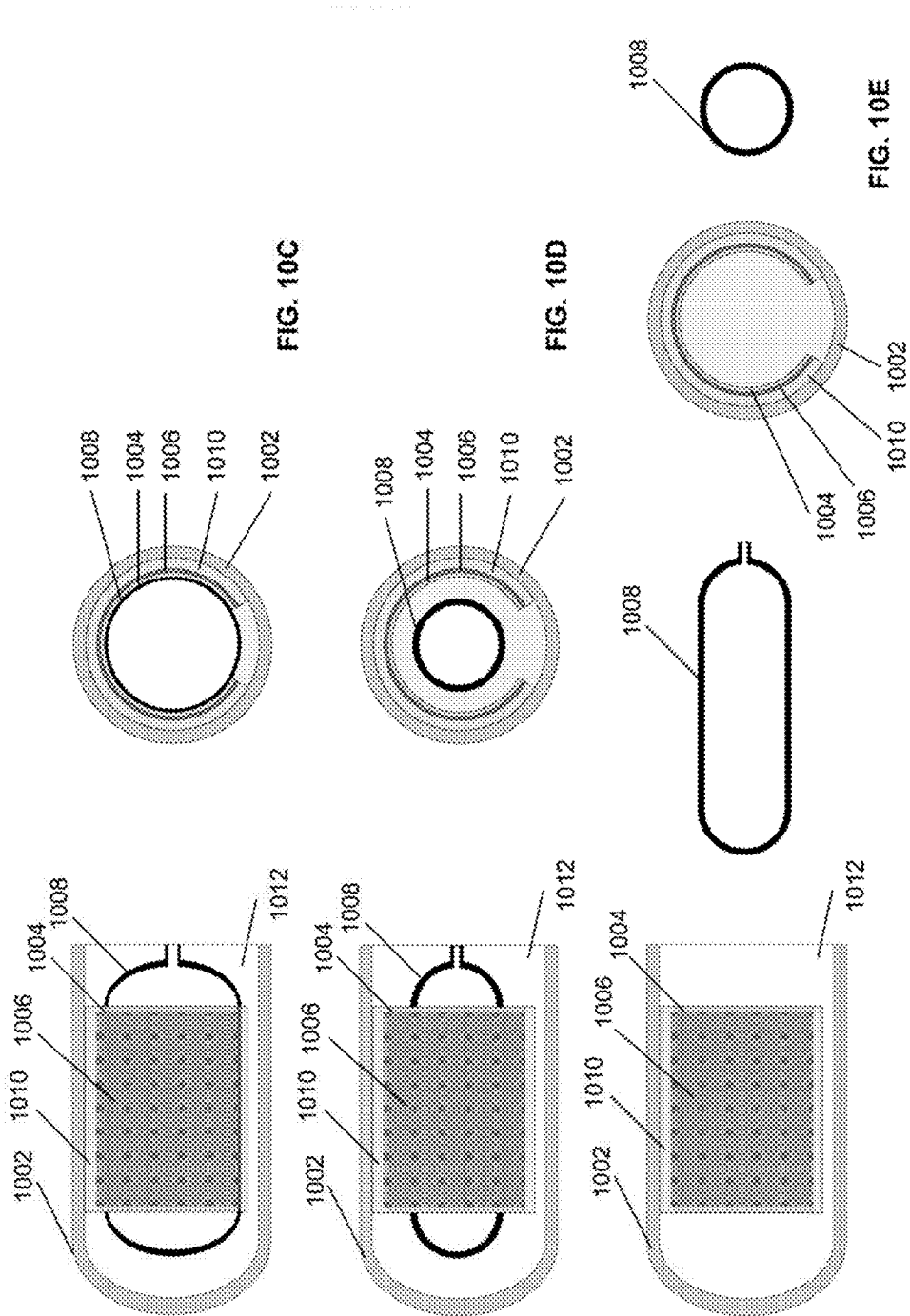

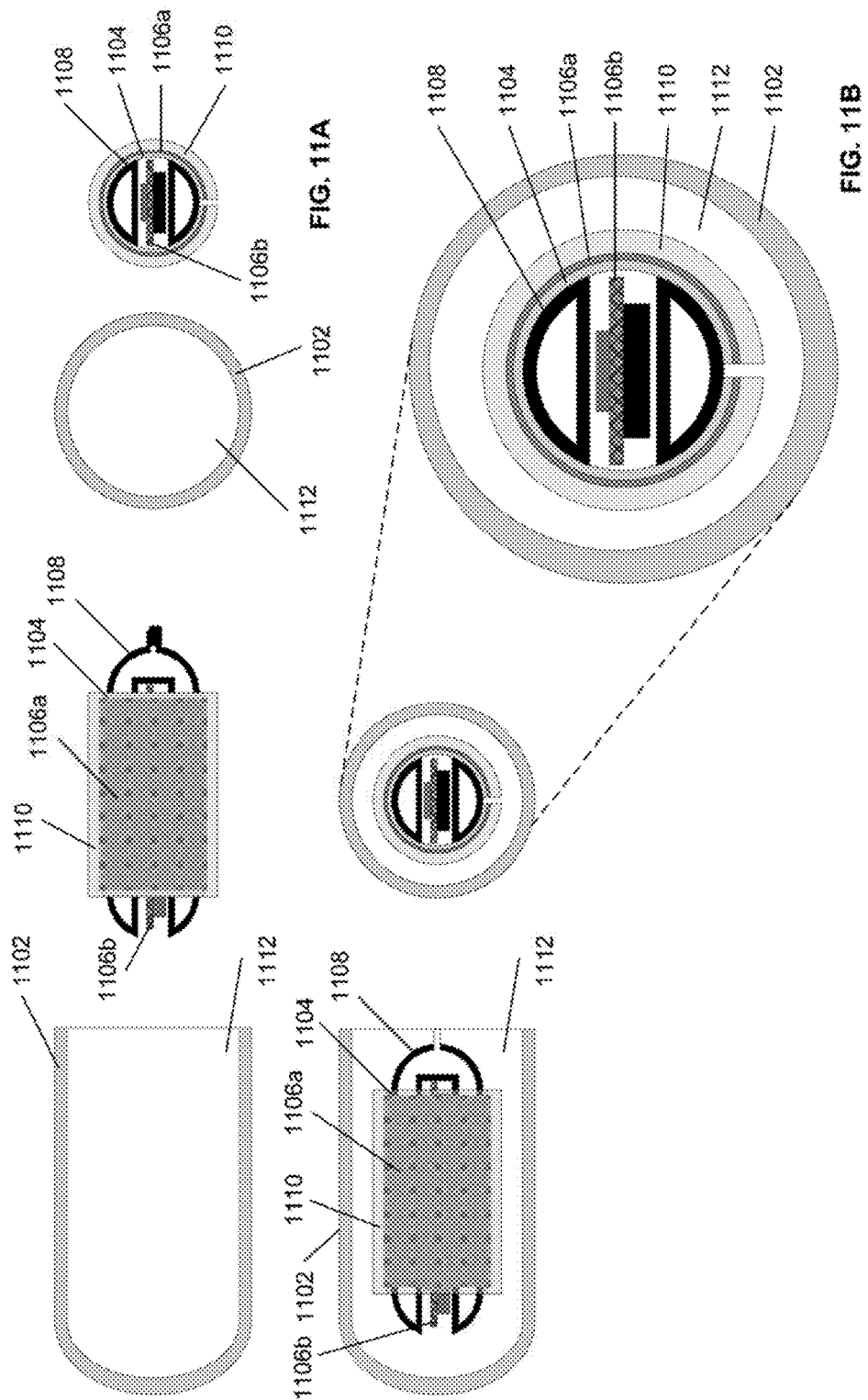

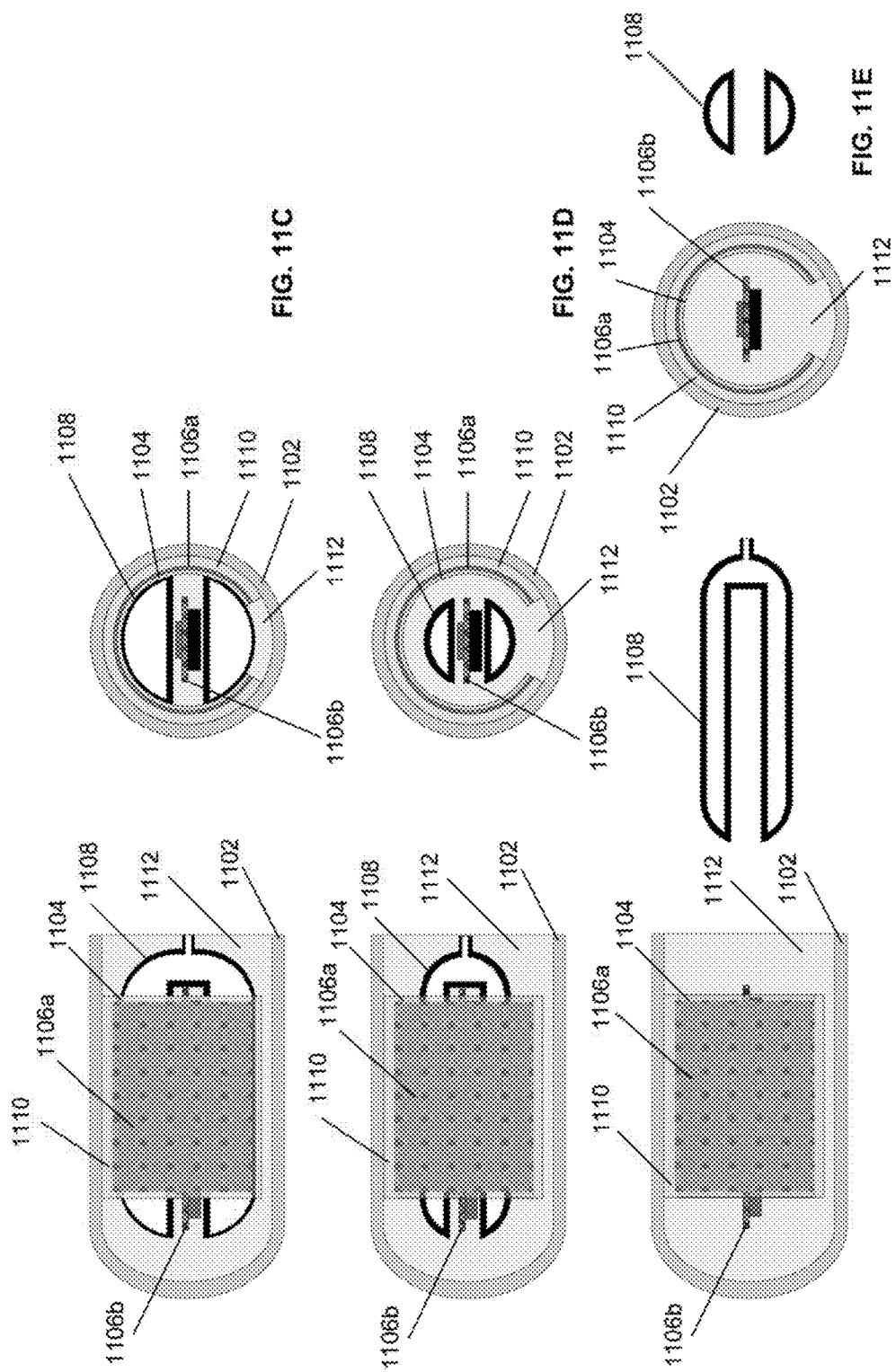

SENSOR DEVICE

CROSS REFERENCE TO RELATED APPLICATION

This application claims the benefit of U.S. patent application No. 62/302,085, "A Sensor Device," filed Mar. 1, 2016, which is assigned to the assignee hereof. The aforementioned United States patent application is hereby incorporated by reference in its entirety.

FIELD

The present disclosure relates to the field of ultrasonic sensors. In particular, the present disclosure relates to embodiments of a sensor device and methods for manufacturing the same.

BACKGROUND

Some conventional ultrasonic transducer devices, such as the devices described in U.S. Pat. No. 5,744,898 and U.S. Pat. No. 8,596,140 B2, tend to be rigid and large in size. These devices are not suited to be adopted as an implantable or ingestible device for non-invasive imaging applications. In some recently improved ultrasound diagnostic imaging devices, such as the devices described in U.S. Patent Application 2014/0276079 A1, require a tube/wire along with the ultrasound transducers to be inserted into a patient. These devices are also unsuitable to be adopted as an implantable or ingestible device for non-invasive imaging applications. In some other ultrasonic transducer devices, such as the devices described in US Patent Application 2011/0130658 A1 and U.S. Pat. No. 8,647,328 B2, are concerned with using the devices, but fail to address the apparatuses and methods for making such devices small with a plurality of flexible ultrasonic transducers, integrated circuits, battery, and printed circuit board such that these components may be packaged into a sensor device for implantable or ingestible device for non-invasive imaging applications. Therefore, there is a need for apparatuses and methods for manufacturing a sensor device that may be adopted as an implantable or ingestible device for non-invasive imaging applications.

SUMMARY

Embodiments of a sensor device and methods for manufacturing the same are disclosed. In one embodiment, a sensor device comprises a piezoelectric micromechanical ultrasonic transducer (PMUT) array configured to transmit and receive ultrasonic signals, where the PMUT array comprises a plurality of PMUTs and the PMUT array is flexible, one or more integrated circuits configured to process the ultrasonic signals, a battery configured to provide power to the PMUT array and the one or more integrated circuits, a coupling material configured to hold the PMUT array, the one or more integrated circuits, and the battery, and a capsule configured to seal the PMUT array, the one or more integrated circuits, the battery and the coupling material within the capsule.

BRIEF DESCRIPTION OF THE DRAWINGS

The aforementioned features and advantages of the disclosure, as well as additional features and advantages thereof, will be more clearly understandable after reading detailed descriptions of embodiments of the disclosure in conjunction with the non-limiting and non-exhaustive aspects of following drawings. The drawings are shown for illustration purposes and they are not drawn to scale. Like numbers are used throughout the figures.

FIGS. 7A-7E illustrate exemplary embodiments of PMUT arrays according to aspects of the present disclosure.

FIGS. 9A-9M illustrate another exemplary implementation of forming a flexible PMUT array for coupling external logic according to aspects of the present disclosure.

FIGS. 10A-10E illustrate a method of manufacturing a sensor device according to aspects of the present disclosure.

FIGS. 11A-11E illustrate a method of manufacturing a sensor device according to aspects of the present disclosure.

DESCRIPTION OF EMBODIMENTS

Embodiments of a sensor device and methods for manufacturing the same are disclosed. The following descriptions are presented to enable any person skilled in the art to make and use the disclosure. Descriptions of specific embodiments and applications are provided only as examples. Various modifications and combinations of the examples described herein will be readily apparent to those skilled in the art, and the general principles defined herein may be applied to other examples and applications without departing from the scope of the disclosure. Thus, the present disclosure is not intended to be limited to the examples described and shown, but is to be accorded the scope consistent with the principles and features disclosed herein. The word "exemplary" or "example" is used herein to mean "serving as an example, instance, or illustration." Any aspect or embodiment described herein as "exemplary" or as an "example" in not necessarily to be construed as preferred or advantageous over other aspects or embodiments.

According to aspects of the present disclosure, the sensor device described herein may be adapted to be an implantable or ingestible device for non-invasive detailed imaging using flexible or rigid PMUT arrays. The sensor device may also be adapted to be a part of wearable devices for monitoring and therapeutic applications. The sensor device may further be adapted to be an endoscope. In some implementations, the sensor device may be fabricated using existing wafer tools or PCB panel tool sets, as well as common glass handling and forming methodologies. In addition, off the shelf printed circuit assembly methods and parts may be used.

Figure 1A:
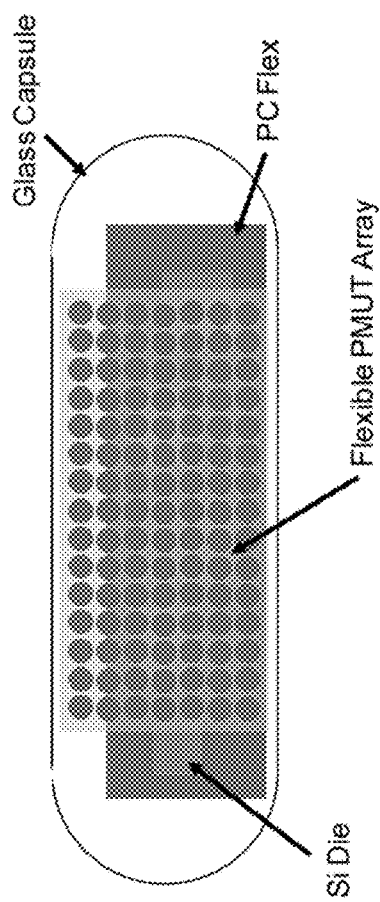
FIGS. 1A-1B illustrate an embodiment of a sensor device according to aspects of the present disclosure.
Figure 1B:
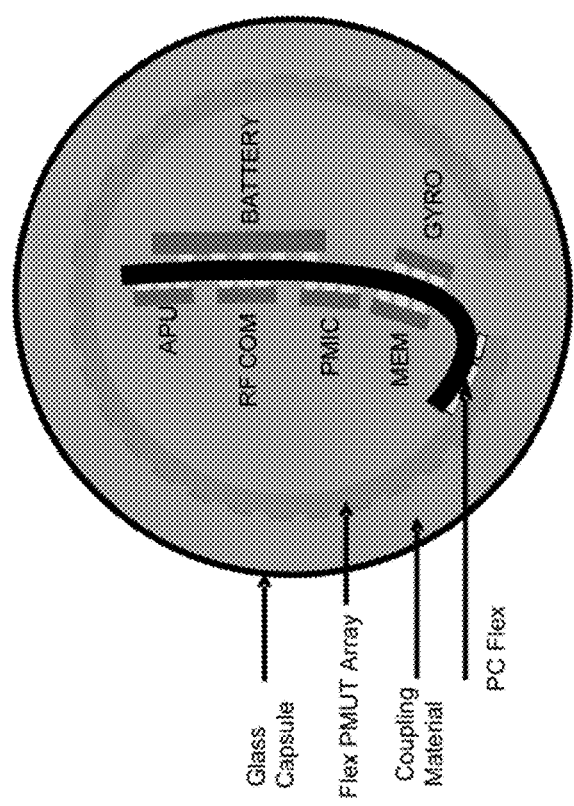

FIGS. 1A-1B illustrate an embodiment of a sensor device according to aspects of the present disclosure. FIG. 1A illustrates a side view and FIG. 1B illustrates an end view of the exemplary sensor device. As shown in FIG. 1A, the sensor device includes a flexible PMUT array, a flexible printed circuit (PC) board, one or more integrated circuits (represented by Si Die), and a capsule. According to aspects of the present disclosure, different materials may be used for the capsule including, but not limited to, glass, ceramic, and titanium. In the end view of the sensor device, in addition to the flexible PMUT array, the flexible PC board, the one or more integrated circuits, and the capsule, the sensor device further includes a battery, and a coupling material. The battery may be configured to provide power to the flexible PMUT array, and the one or more integrated circuits. The one or more integrated circuits may include accelerated processing units (APUs), radio frequency communications components (RF COM), power management integrated circuits (PMIC), dynamic and static memories (MEM), gyroscopic sensor integrated circuits (GYRO), other types of sensors, or other integrated circuits. The coupling material may be configured to hold the flexible PMUT array, the flexible PC board, the battery, and the one or more integrated circuits in place with respect to the capsule. In some implementations, the battery may be charged wirelessly via ultrasonic waves or radio frequency waves. The capsule may be configured to seal the flexible PMUT array, the flexible PC board, the battery, the one or more integrated circuits, and the coupling material within the capsule.

According to aspects of the present disclosure, the flexible PC board (also referred to as PC flex) may be bonded to flexible PMUT array (FPA) using anisotropic conductive film (ACF), solder paste, or other methods. If a surface mount battery is not used, connect leads of cylindrical battery may be soldered to the flexible PC board. If surface mount battery is used, flexible PC board and the FPA may be rolled around a cylindrical holder (or battery), and the components may be clamped/tacked together into a coiled assembly. Inside of the capsule may be coated with a thin layer of coupling material (such as polyimide or similar) and the coupling material may be partially cured (with UV or thermal). The coiled assembly may be inserted into the capsule (which has at least one end open) and then the coiled assembly may be released inside the capsule. Thereafter, the capsule may be filled with a coupling material or molding material and may be cured completely (for example, using 150 degrees C. snap cure or UV safe for insert assembly). In addition, open end(s) of the capsule may be sealed (or molded) using heat. Note that local heating may be controlled in such a way that the inserted assembly would not be damaged in the sealing step.

Figure 2A:
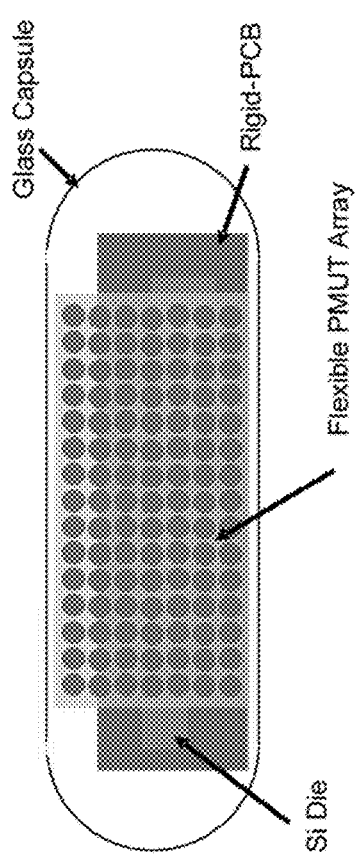
FIGS. 2A-2B illustrate another embodiment of a sensor device according to aspects of the present disclosure.
Figure 2B:
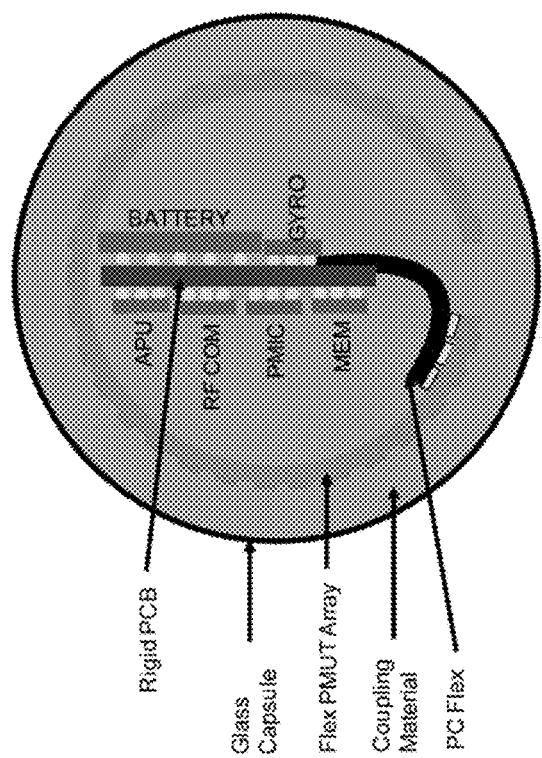

FIGS. 2A-2B illustrate another embodiment of a sensor device according to aspects of the present disclosure. FIG. 2A illustrates a side view and FIG. 2B illustrates an end view of the exemplary sensor device. In the example shown in FIG. 2A the sensor device includes a flexible PMUT array, a rigid printed circuit (PC) board, one or more integrated circuits (represented by Si Die), and a capsule. In the end view of the sensor device shown in FIG. 2B, in addition to the flexible PMUT array, the rigid PC board, the one or more integrated circuits, and the capsule, the sensor device further includes a battery, and a coupling material. The battery may be configured to provide power to the flexible PMUT array, and the one or more integrated circuits. The one or more integrated circuits may include APU, RF COM, PMIC, MEM, GYRO, etc. The coupling material may be configured to hold the flexible PMUT array, the rigid PC board, the battery, and the one or more integrated circuits in place with respect to the capsule. The capsule may be configured to seal the flexible PMUT array, the rigid PC board, the battery, the one or more integrated circuits, and the coupling material within the capsule.

Figure 3A:
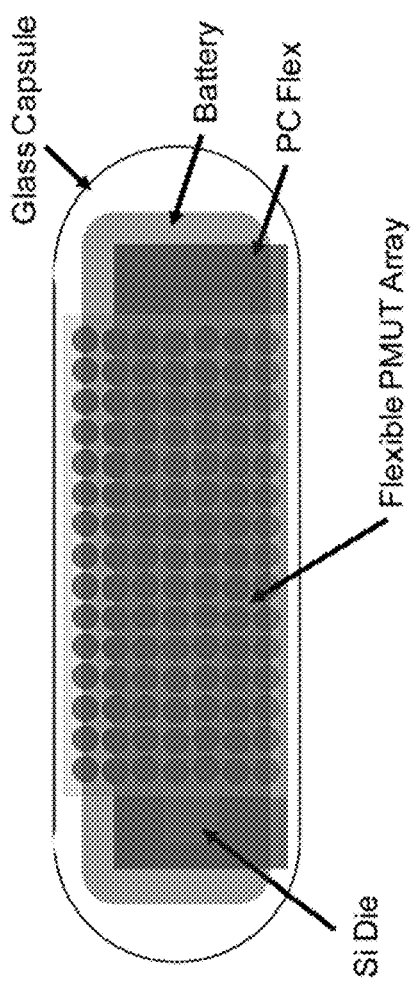
FIGS. 3A-3B illustrate yet another embodiment of a sensor device according to aspects of the present disclosure.
Figure 3B:
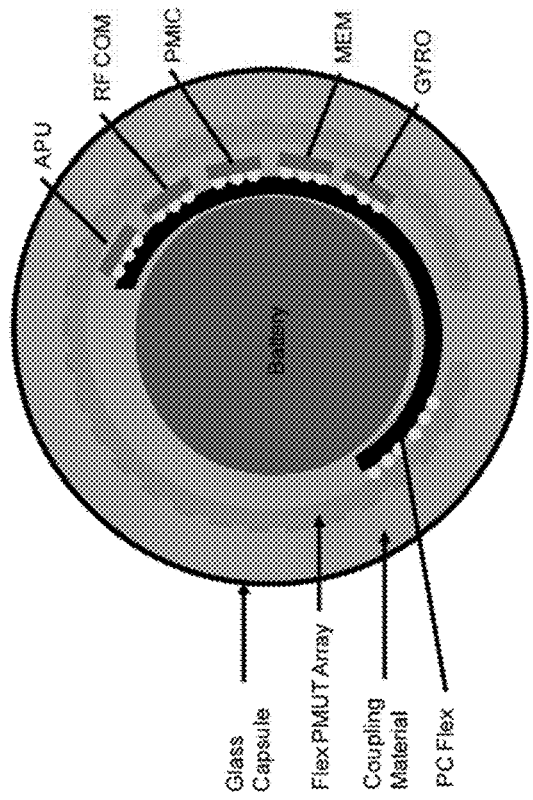

FIGS. 3A-3B illustrate yet another embodiment of a sensor device according to aspects of the present disclosure. FIG. 3A illustrates a side view and FIG. 3B illustrates an end view of the exemplary sensor device. In the example shown in FIG. 3A, the sensor device includes a flexible PMUT array, a flexible printed circuit (PC) board, one or more integrated circuits (represented by Si Die), a battery, and a capsule. In the end view of the sensor device shown in FIG. 3B, in addition to the flexible PMUT array, the flexible PC board, the one or more integrated circuits, the battery and the capsule, the sensor device further includes a coupling material. The battery may be configured to provide power to the flexible PMUT array, and the one or more integrated circuits. The one or more integrated circuits may include APU, RF COM, PMIC, MEM, GYRO, etc. The coupling material may be configured to hold the flexible PMUT array, the flexible PC board, the battery, and the one or more integrated circuits in place with respect to the capsule. The capsule may be configured to seal the flexible PMUT array, the flexible PC board, the battery, the one or more integrated circuits, and the coupling material within the capsule.

Figure 4A:
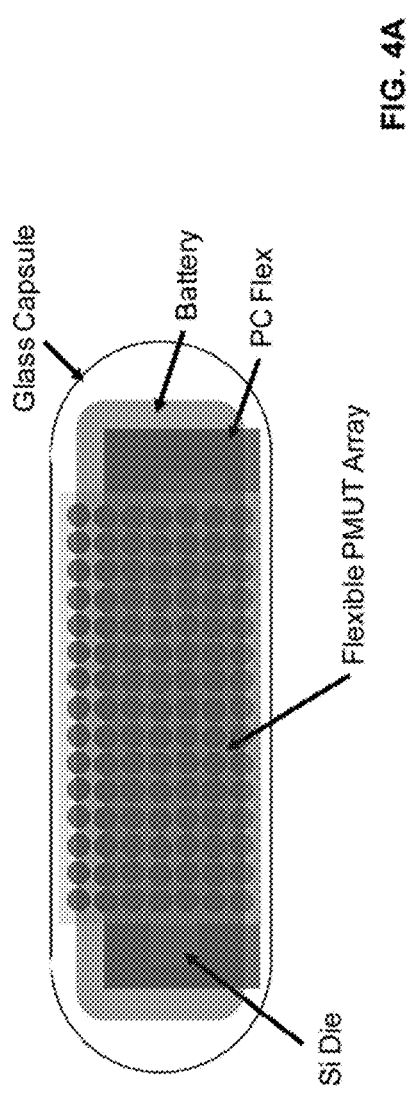
FIGS. 4A-4B illustrate yet another embodiment of a sensor device according to aspects of the present disclosure.
Figure 4B:
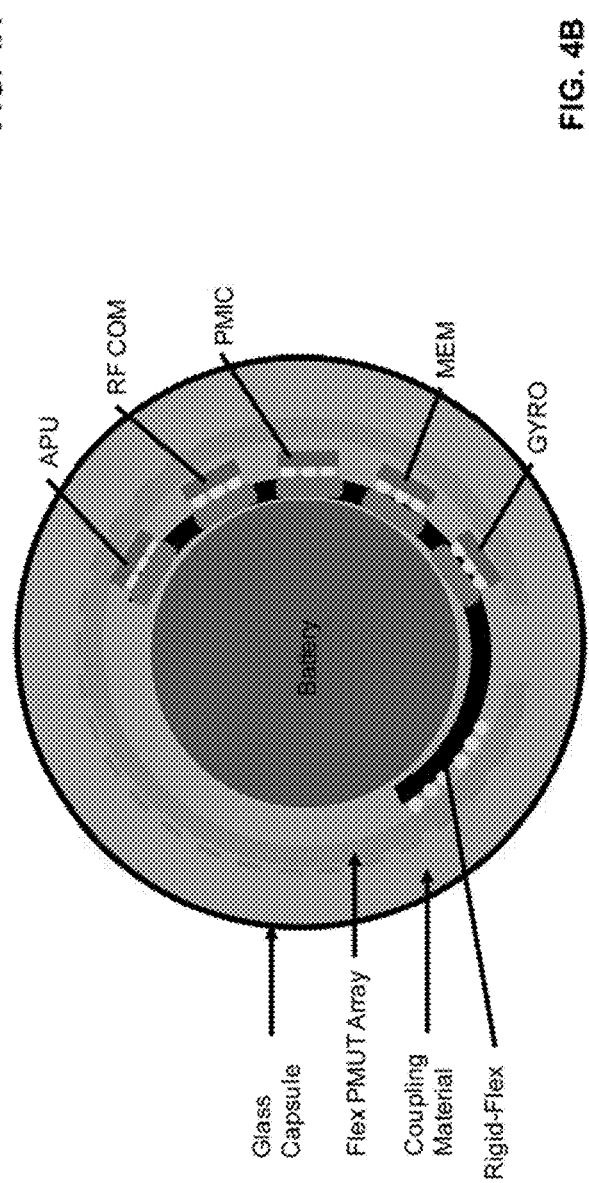

FIGS. 4A-4B illustrate yet another embodiment of a sensor device according to aspects of the present disclosure. FIG. 4A illustrates a side view and FIG. 4B illustrates an end view of the exemplary sensor device. In the example shown in FIG. 4A, the sensor device includes a flexible PMUT array, a rigid-flexible printed circuit (PC) board (also referred to as rigid-flex), one or more integrated circuits (represented by Si Die), a battery, and a capsule. In the end view of the sensor device shown in FIG. 4B, in addition to the flexible PMUT array, the rigid-flexible PC board, the one or more integrated circuits, the battery and the capsule, the sensor device further includes a coupling material. The battery may be configured to provide power to the flexible PMUT array, and the one or more integrated circuits. The one or more integrated circuits may include APU, RF COM, PMIC, MEM, GYRO, etc. The coupling material may be configured to hold the flexible PMUT array, the rigid-flexible PC board, the battery, and the one or more integrated circuits in place with respect to the capsule. The capsule may be configured to seal the flexible PMUT array, the rigid-flexible PC board, the battery, the one or more integrated circuits, and the coupling material within the capsule.

Figure 5A:
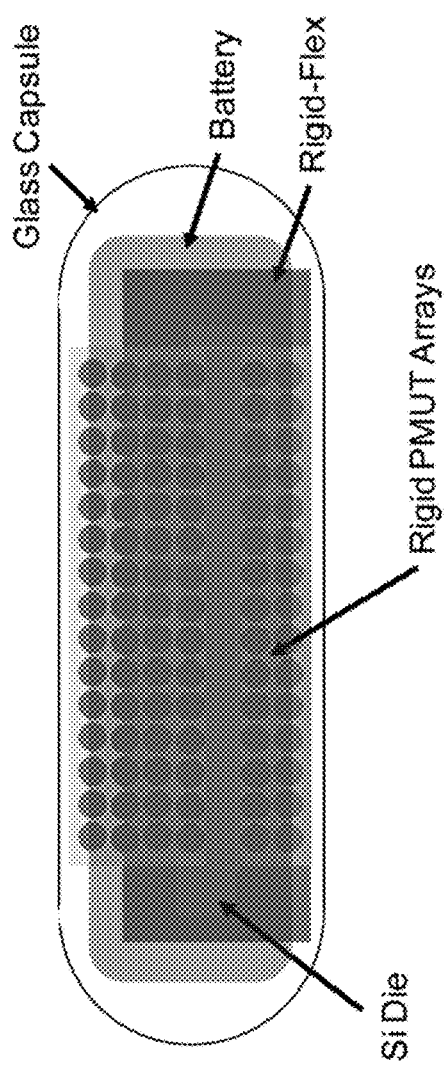
FIGS. 5A-5B illustrate yet another embodiment of a sensor device according to aspects of the present disclosure.
Figure 5B:
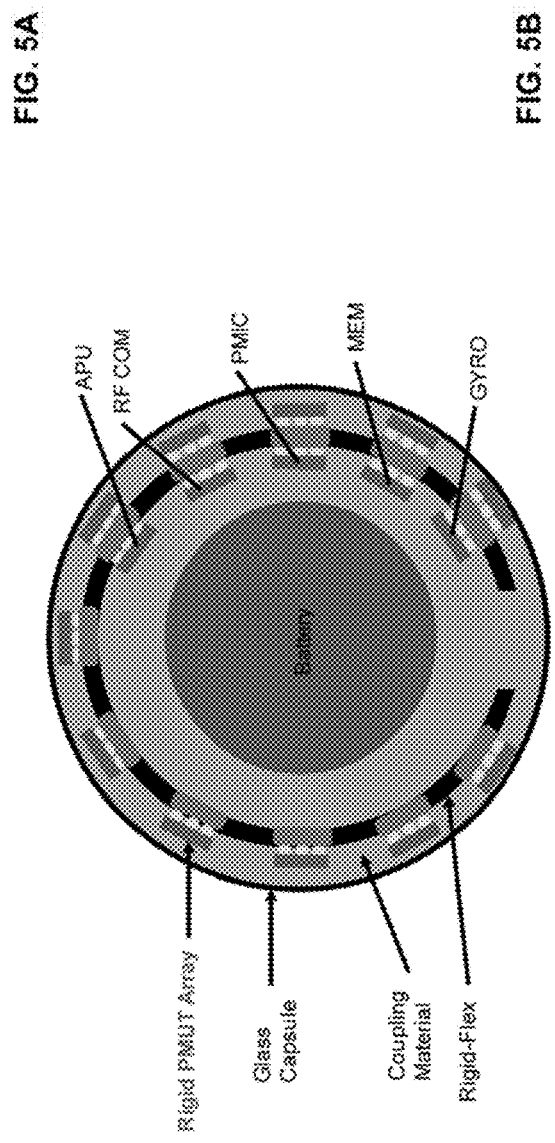

FIGS. 5A-5B illustrate yet another embodiment of a sensor device according to aspects of the present disclosure. FIG. 5A illustrates a side view and FIG. 5B illustrates an end view of the exemplary sensor device. In the example shown in FIG. 5A, the sensor device includes multiple rigid PMUT arrays, a rigid-flexible printed circuit (PC) board, one or more integrated circuits (represented by Si Die), a battery, and a capsule. In the end view of the sensor device shown in FIG. 5B, in addition to the multiple rigid PMUT arrays, the rigid-flexible PC board, the one or more integrated circuits, the battery and the capsule, the sensor device further includes a coupling material. The battery may be configured to provide power to the multiple rigid PMUT arrays, and the one or more integrated circuits. The one or more integrated circuits may include APU, RF COM, PMIC, MEM, GYRO, etc. The coupling material may be configured to hold the multiple rigid PMUT arrays, the rigid-flexible PC board, the battery, and the one or more integrated circuits in place with respect to the capsule. The capsule may be configured to seal the multiple rigid PMUT arrays, the rigid-flexible PC board, the battery, the one or more integrated circuits, and the coupling material within the capsule.

Figure 6A:
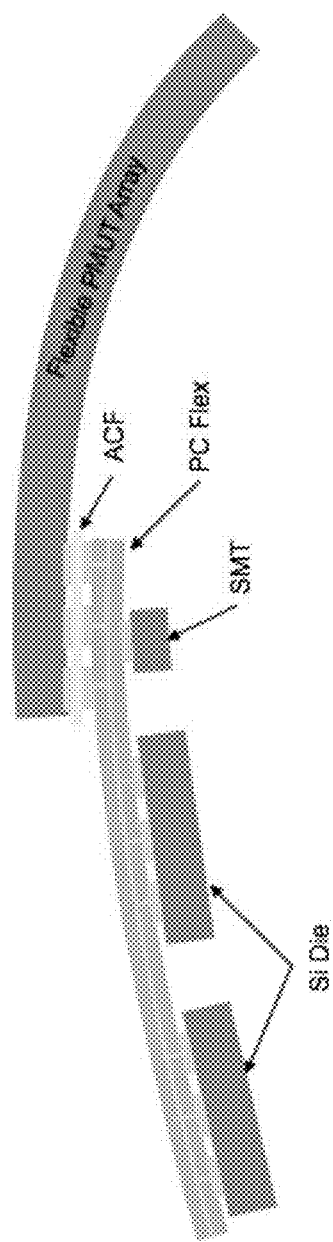
FIGS. 6A-6D illustrate exemplary implementations of coupling one or more integrated circuits to a PMUT array according to aspects of the present disclosure.

FIGS. 6A-6D illustrate exemplary implementations of coupling one or more integrated circuits to a PMUT array according to aspects of the present disclosure. FIG. 6A illustrates an example of integrating a flexible PMUT array with multiple chip modules (also referred to as one or more integrated circuits, represented by Si Die and surface mount transistor(s) SMT) on a flexible PC board. The flexible PMUT array may be electrically connected to the flexible PC board using ACF. In some implementations, other interconnect solutions, such as solder paste, may be used.

Figure 6B:
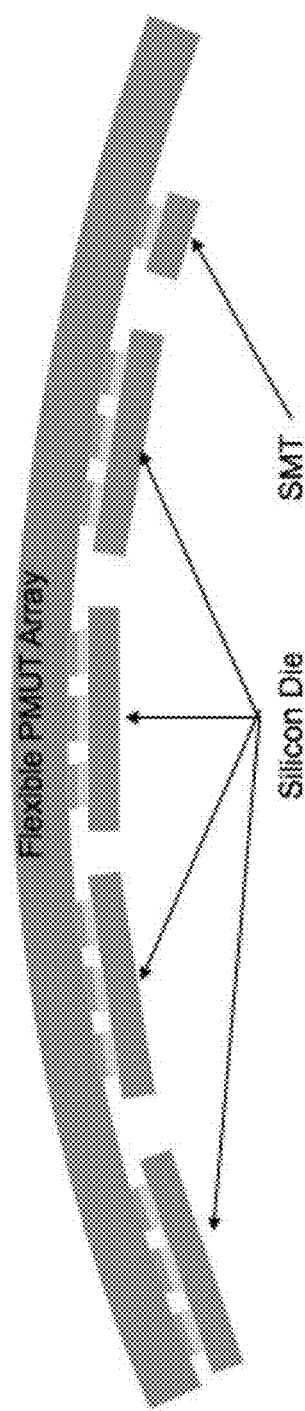

FIG. 6B illustrates an example of integrating a flexible PMUT array with multiple chip modules directly onto the backside of the flexible PMUT. The flexible PMUT array may be electrically connected to the multiple chip modules using various flexible interconnect solutions, such as ACF, solder paste, etc.

Figures 6C, 6D:
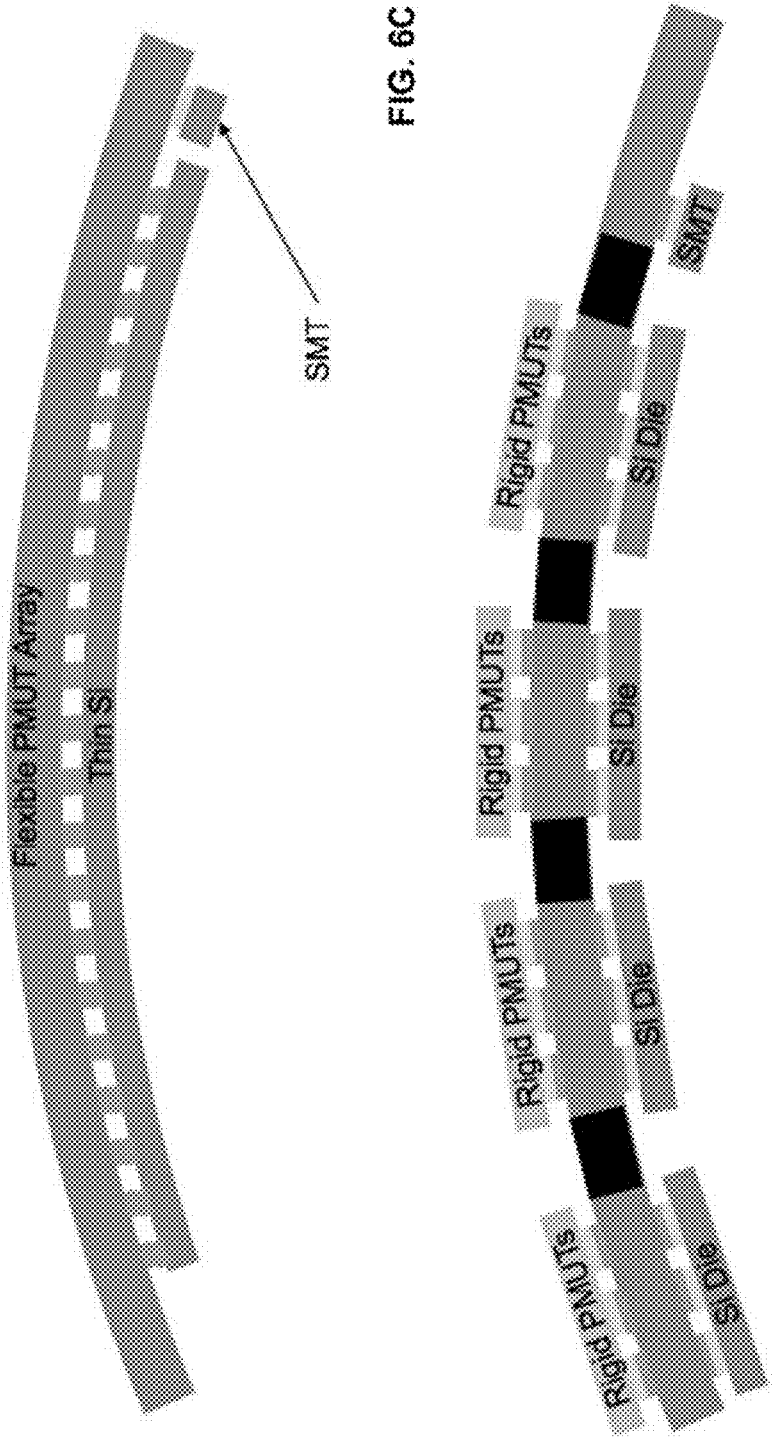

FIG. 6C illustrates an example of integrating a flexible PMUT array with multiple chip modules directly onto the backside of the flexible PMUT. In this example, one or more chip modules may be implemented as thin silicon (Thin Si). The flexible PMUT array may be electrically connected to the thin silicon using various flexible interconnect solutions, such as ACF, solder paste, etc.

FIG. 6D illustrates an example of integrating rigid PMUT arrays with one or more integrated circuits (represented as Si Die and SMT) using a rigid-flexible PC board. In this example, some sections of the rigid-flexible PC board may be rigid, which may be used for attaching the rigid PMUTs and Si Die. Some other sections of the rigid-flexible PC board may be flexible, allowing the rigid-flexible PC board to bend and conform to a desired shape.

Figure 7E:
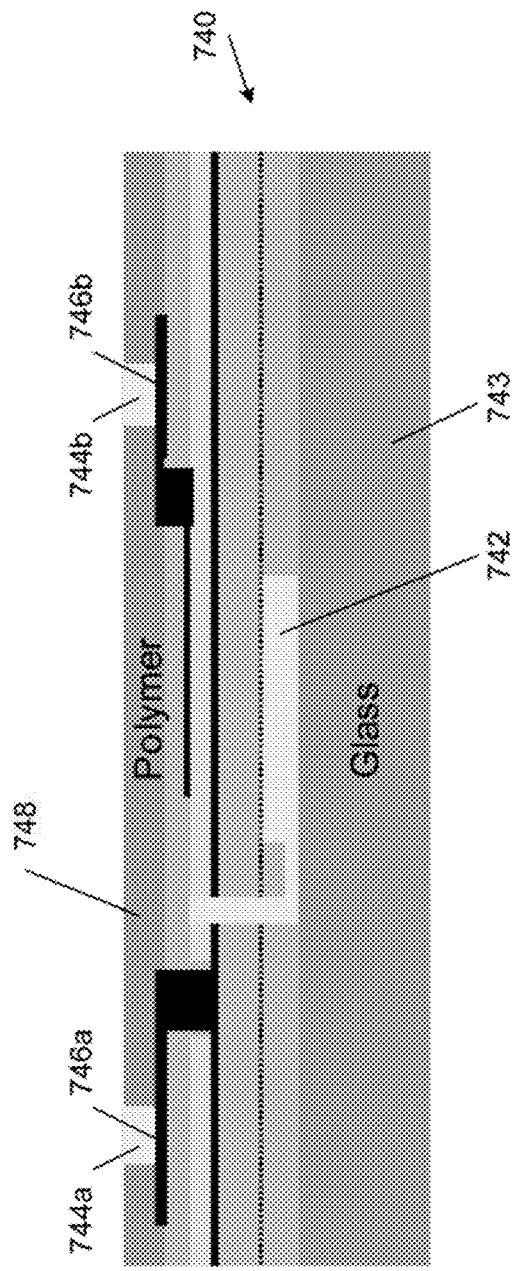

FIGS. 7A-7E illustrate exemplary embodiments of PMUT arrays according to aspects of the present disclosure. FIG. 7A illustrates an example of a PMUT 700 that can be replicated to form a flexible PMUT array. In this exemplary implementation, the cavity 702 of the PMUT may be concealed with different types of polymer materials (708a and 708b) on both the front side and the back side of the PMUT 700. Vias (704a and 704b) and electrodes (706a and 706b) may be provided to allow the PMUT 700 to be accessed and controlled.

FIG. 7B illustrates an example of another PMUT 710 that may be replicated to form a flexible PMUT array. In this exemplary implementation, the cavity 712 of the PMUT may be opened through an opening of a polymer material 718b on the back side of the PMUT. The front side of the PMUT is covered with a polymer layer 718a. Vias (714a and 714b) and electrodes (716a and 716b) may be provided to allow the PMUT 710 to be accessed and controlled.

FIG. 7C illustrates an example of yet another PMUT that may be replicated to form a flexible PMUT array. In this exemplary implementation, the cavity 722 of the PMUT 720 may be concealed on both the front side and the back side of the PMUT 720. In addition to polymer layers (728a and 728b) covering the front side and the back side of the PMUT 720, a third polymer layer (728c) may be deposited to cover the polymer layer 728a. Vias (724a and 724b) and electrodes (726a and 726b) may be provided to allow the PMUT 720 to be accessed and controlled.

FIG. 7D illustrates an example of yet another PMUT that may be replicated to form a flexible PMUT array. In this exemplary implementation, the cavity 732 of the PMUT may be opened on the back side of the PMUT 730. In addition to polymer layers (738a and 738b) covering the front side and the back side of the PMUT 720 respectively, a third polymer layer (738c) may be deposited on the front side of the PMUT 730. Vias (734a and 734b) and electrodes (736a and 736b) may be provided to allow the PMUT 730 to be accessed and controlled.

FIG. 7E illustrates an example of yet another PMUT that may be replicated to form a rigid PMUT array. In this exemplary implementation, the cavity 742 of the PMUT 740 may be concealed on both the front side and the back side of the PMUT 740. The front side of the PMUT 740 is covered with a polymer layer 748. A layer of rigid material 743, such as glass, may be attached to the back side of the PMUT. Vias (744a and 744b) and electrodes (746a and 746b) may be provided to allow the PMUT 740 to be accessed and controlled.

According to aspects of the present disclosure, the following table provides names, their corresponding definitions and exemplary materials that may be used for the various layers of a PMUT as described in FIGS. 8A-8P and FIG. 9A-9M. The contents of the table show certain exemplary implementations. Different implementations, such as M1 may be used as an electrode for signal while M2 may be used as an electrode for circuit ground may be implemented. In addition, different materials may be used to construct the different layers of the PMUT, in addition to the materials shown in the table.

| Layer Name | Function/Definition | Exemplary Material(s) |
| --- | --- | --- |
| SUB | Rigid substrate | Glass, Silicon |
| CAR | Carrier substrate | Glass, Silicon, PCB core |
| REL | Release layer for carrier | UV release adhesive |
| PL1 | Base planarization layer | Oxide (polished/plasma etched) |
| PT | Platten/mechanical membrane | Oxide |
| ENC | Encapsulation/passivation | Oxide |
| SEn | Laminated polymer layer | Photo image-able polymer |
| M1 | Bottom electrode (Ground plane) | Moly |
| M2 | Top electrode (Signal) | Moly/Aluminum |
| M3 | Routing/pads | Aluminum (could be plated Cu) |
| A2 | Piezoelectric material | Aluminum Nitride (200 deg. C.) |
| V1 | Membrane release via | Via to allow release of membrane cavity |
| V2 | Electrode contact vias | Contact vias for M1/M2 electrodes |
| VP | Pad vias | Via to open passivation for contact to M3 |
| S1 | Cavity release layer | a-Si (may be Mo or polymer) |
| E1 | Encapsulation layer | |

FIGS. 8A-8P illustrate an exemplary implementation of forming a flexible PMUT array for coupling to external logic according to aspects of the present disclosure. In this exemplary implementation, FIG. 8A illustrates an example of coating a glass carrier (labeled as CAR) with a release film (labeled as REL). FIG. 8B illustrates an example of patterning redistribution layer (labeled as M0) metal and pads. FIG. 8C illustrates an example of laminating a planarization polymer layer (labeled as SE1).

FIG. 8D illustrates an example of opening and filling contact vias to create pads (labeled as V0) at the top of the base polymer layer. FIG. 8E illustrates an example of depositing a sacrificial material (labeled as S1), which may be patterned and etched to define a cavity of the PMUT. FIG. 8F illustrates an example of depositing an oxide layer (labeled as PL1) and performing planarization using chemical-mechanical planarization or etch-back.

FIG. 8G illustrates an example of depositing an oxide mechanical layer (labeled as PT). FIG. 8H illustrates an example of depositing a piezoelectric stack, including a bottom electrode (labeled as M1), a piezoelectric material (labeled as A2), and a top electrode (labeled as M2).

FIG. 8I illustrates an example of forming patterns on M1, M2, and A2. FIG. 8J illustrates an example of depositing a passivation layer (labeled as SE2) and opening release vias.

FIG. 8K illustrates an example of forming contact through etching. FIG. 8L illustrates an example of forming a top redistribution layer.

FIG. 8M illustrates an example of etching a release via. FIG. 8N illustrates an example of removing sacrificial material to form a cavity through etching.

Figure 8O:
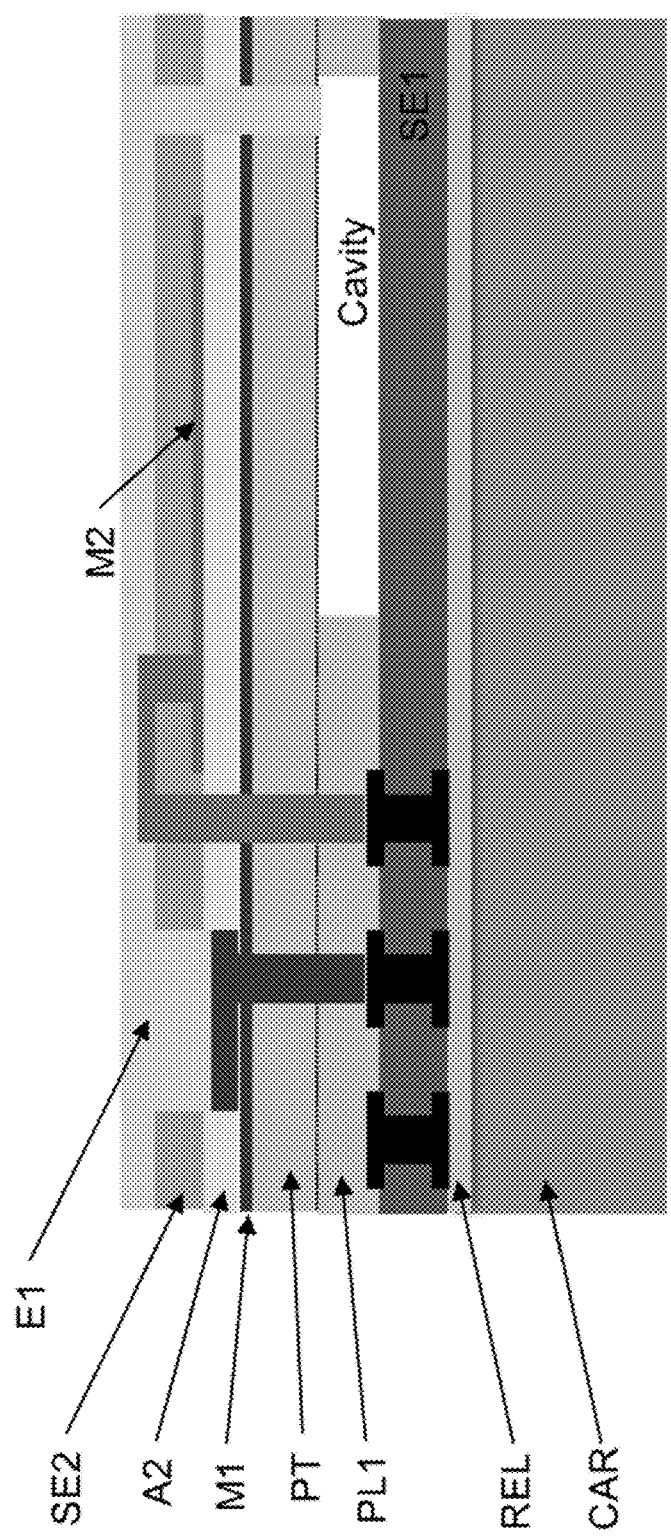
FIGS. 8A-8P illustrate an exemplary implementation of forming a flexible PMUT array for coupling external logic according to aspects of the present disclosure.

FIG. 8O illustrates an example of forming an encapsulation (labeled as E1). FIG. 8P illustrates an example of forming the flexible PMUT by releasing the carrier. The flexible PMUT array formed through this process may be used to enable attachment of external logics from the backside of the PMUT using pads and a redistribution layer for routing.

Figure 9I:
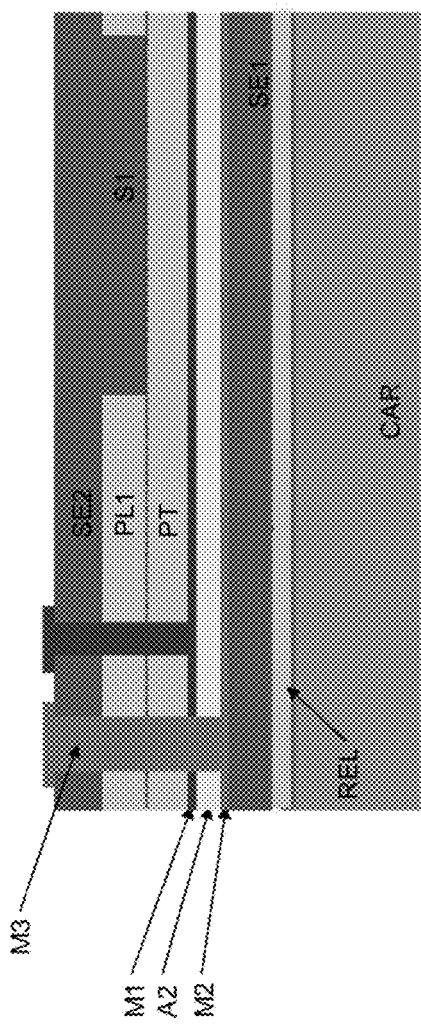

FIGS. 9A-9M illustrate another exemplary implementation of forming a flexible PMUT array for coupling to external logic according to aspects of the present disclosure. In this exemplary implementation, FIG. 9A illustrates an example of coating a glass carrier (labeled as CAR) with a release film (labeled as REL). FIG. 9B illustrates an example of laminating planarization polymer layer (labeled as SE1). FIG. 9C illustrates an example of depositing a piezoelectric stack, including a bottom electrode (labeled as M1), a piezoelectric material (labeled as A2), and a top electrode (labeled as M2).

FIG. 9D illustrates an example of forming contact vias to access the electrodes. FIG. 9E illustrates an example of depositing a mechanical layer (labeled as PT). FIG. 9F illustrates an example of depositing a sacrificial material (labeled as S1), which may be patterned and etched to define a cavity of the PMUT.

FIG. 9G illustrates an example of laminating a second encapsulation layer (labeled SE2) and opening initial vias for accessing the electrodes. FIG. 9H illustrates an example of etching contact vias for accessing the electrodes.

Figure 9J:
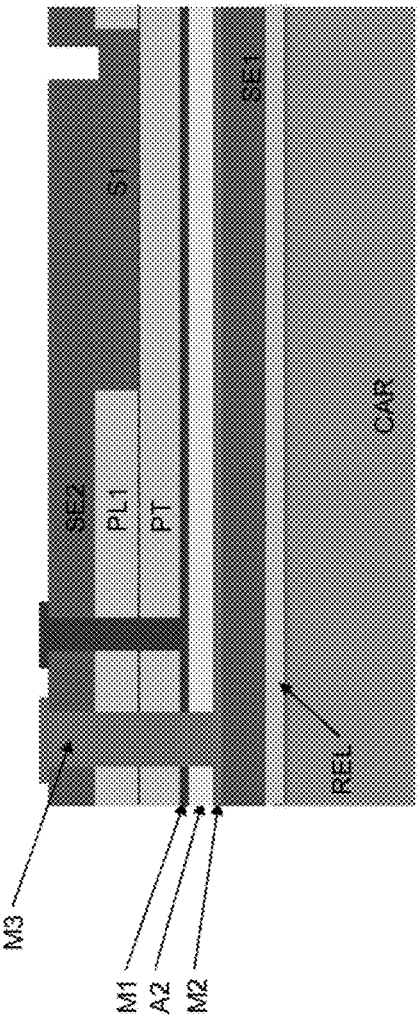

FIG. 9I illustrates an example of forming metal redistribution layers. FIG. 9J illustrates an example for opening release via.

Figure 9K:
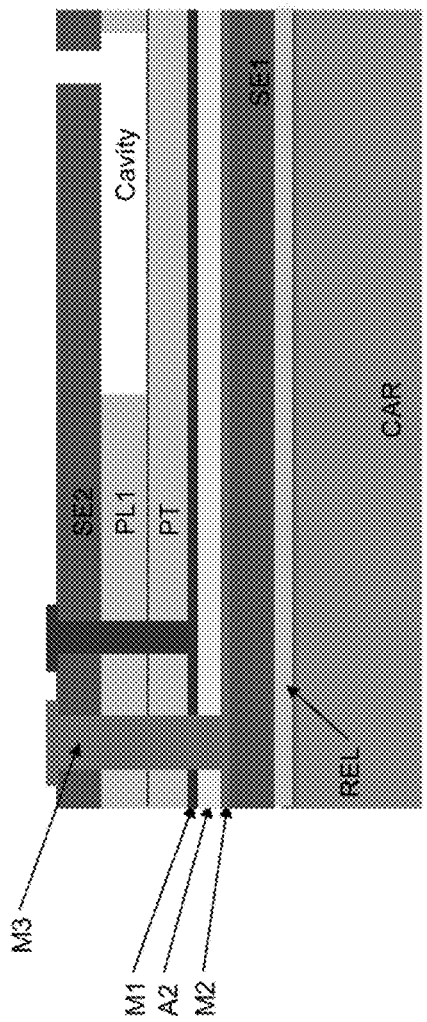
Figure 9L:
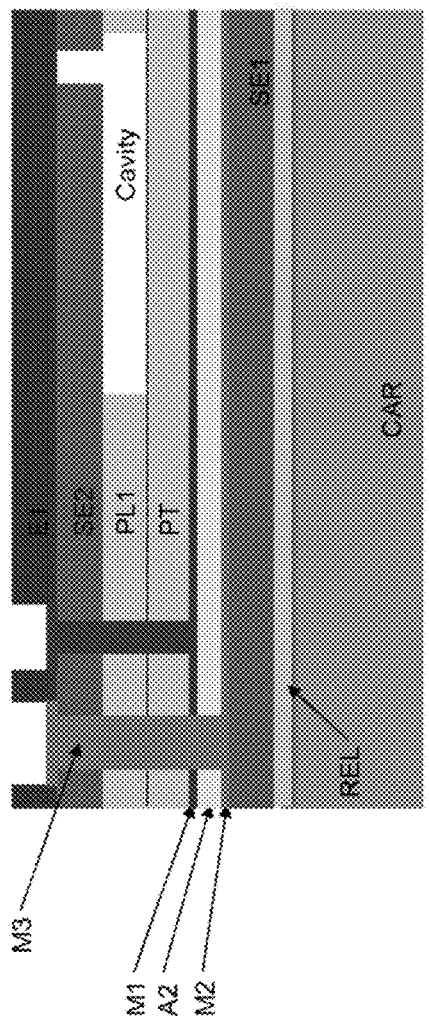

FIG. 9K illustrates an example of removing sacrificial material to form a cavity through etching. FIG. 9L illustrates an example of forming an encapsulation layer (labeled as E1) and forming pad vias.

Figure 9M:
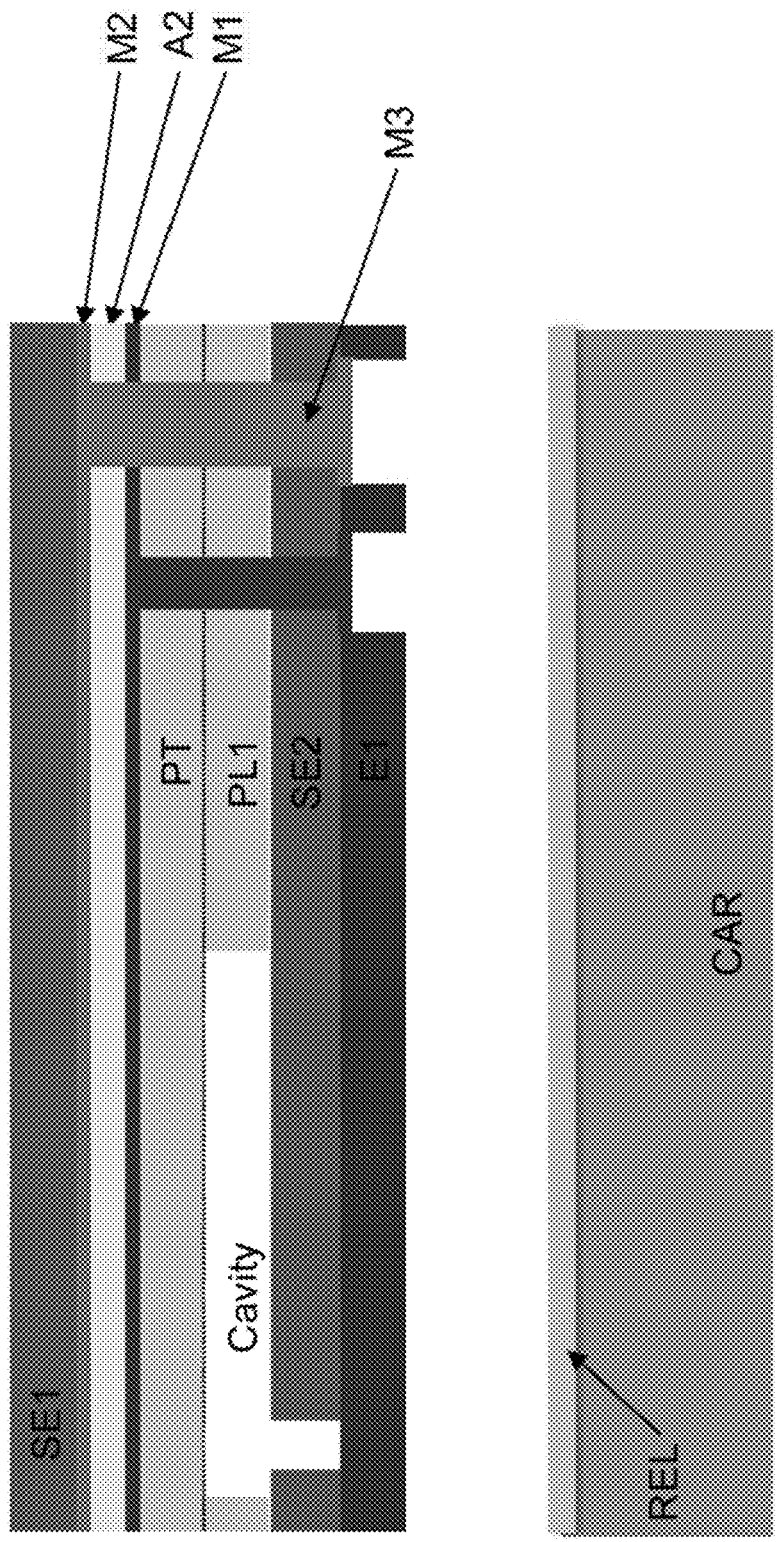

FIG. 9M illustrates an example of forming the flexible PMUT by releasing the carrier. In this example, the PMUT formed from the steps of FIG. 9A to FIG. 9L is turned upside down. The flexible PMUT array formed through this process may be used to enable attachment of external logics from the backside of the PMUT using pads and a redistribution layer for routing.

FIGS. 10A-10E illustrate a method of manufacturing a sensor device according to aspects of the present disclosure. In FIG. 10A, on the left hand side, a side view of a capsule 1002, a flexible PMUT array 1004, electronic components 1006, an inflatable device 1008, and a coupling material 1010 of the sensor device are shown, respectively. On the right hand side, a cross sectional view of the capsule 1002, the flexible PMUT array 1004, the electronic components 1006, the inflatable device 1008, and the coupling material 1010 of the sensor device are shown, respectively. Numeral 1012 may represent an air gap. The flexible PMUT array 1004 and the electronic components 1006 may be attached to one another as described in FIG. 6A to FIG. 6D.

The flexible PMUT array 1004 and the electronic components 1006 may be wrapped around the inflatable device 1008 (also referred to as a bladder). In one embodiment, the inflatable device 1008 may have a cylindrical shape, with an opening at one end. The capsule 1002 may be configured to encapsulate the flexible PMUT array 1004 and the electronic components 1006. FIG. 10A shows the view of the flexible PMUT array 1004, the electronic components 1006, the inflatable device 1008, and other related components (not shown) prior to being inserted into the capsule 1002. In some implementations, the other related components may include, but not limited to, battery, flexible printed circuit board, rigid-flexible printed circuit board, or some combinations thereof. Each layer of the cross sectional view is described below in the description of FIG. 10B.

In FIG. 10B, on the left hand side, a side view of the flexible PMUT array 1004, the electronic components 1006, the inflatable device 1008, the coupling material 1010, and other related components after they are being inserted into the capsule 1002 is shown. In the middle, a cross sectional view of the flexible PMUT array 1004, the electronic components 1006, the inflatable device 1008, the coupling material 1010, and other related components after they are being inserted into the capsule 1002 is shown. On the right hand side, an enlarged cross sectional view is shown.

In some implementations, moving from inside to outside in the enlarged cross sectional view, the inner most layer may be the inflatable device 1008; the next layer may be the flexible PMUT array 1004; the next layer may be the electronic components 1006; the next layer may be the coupling material 1010 (also referred to as bonding material); the next layer may be an air gap 1012; and the outer most layer is the capsule 1002. In some other implementations, the position of the flexible PMUT array 1004 and the electronic components 1006 may be interchangeable.

In FIG. 10C, the inflatable device 1008 may be inflated to a predetermined pressure so that it is configured to push the flexible PMUT array 1004, the electronic components 1006, and the coupling material 1010 against the inner wall of the capsule 1002. On the left hand side, a side view of the flexible PMUT array 1004, the electronic components 1006, the inflatable device 1008, the coupling material 1010, and other related components after they are being pushed against the inner wall of the capsule 1002 is shown. On the right hand side, a cross sectional view of the flexible PMUT array 1004, the electronic components 1006, the inflatable device 1008, the coupling material 1010, and other related components after they are being pushed against the inner wall of the capsule 1002 is shown.

Note that the air gap 1012 between the coupling material 1010 and the inner wall of the capsule 1002 may be substantially removed by the process of inflating the inflatable device 1008. The coupling material 1010 may then be cured, for example by heat, UV light, or through other means. As a result of the curing process, the flexible PMUT array 1004, the electronic components 1006, and other related components may be firmly attached to the inner wall of the capsule 1002.

In FIG. 10D, the inflatable device 1008 may then be deflated. On the left hand side, a side view of the inflatable device 1008 after it is being deflated is shown. On the right hand side, a cross sectional view of the inflatable device 1008 after it is being deflated is shown. FIG. 10E shows the side view and the cross sectional view of the sensor device with the flexible PMUT array 1004, the electronic components 1006, and other related components being attached to the inner wall of the capsule 1002 using the coupling material 1010. After the inflatable device 1008 has been removed, the capsule 1002 may then be sealed.

FIGS. 11A-11E illustrate a method of manufacturing a sensor device according to aspects of the present disclosure. In FIG. 11A, on the left hand side, a side view of a capsule 1102, a flexible PMUT array 1104 and electronic components 1106a and 1106b, an inflatable device 1108, and a coupling material 1110 of the sensor device are shown, respectively. On the right hand side, a cross sectional view of the capsule 1102, the flexible PMUT array 1104 and electronic components 1106a and 1106b, the inflatable device 1108, and the coupling material 1110 of the sensor device are shown, respectively. Numeral 1112 may represent an air gap. The flexible PMUT array 1104 and the electronic components 1106a and 1106b may be attached to one another as described in FIG. 6A to FIG. 6D.

Note that the electronic components 1106a and 1106b may have different physical forms than those shown in FIG. 11A. Instead of having the electronic components being wrapped around an inflatable device 1108 (also referred to as a bladder), they may be held in the center of the sensor device in some implementations. Note that the connection between the electronic components and the PMUT array is not shown in FIGS. 11A-11E.

The inflatable device 1108 may have a sandwich shape to hold the electronic components in the middle, with an opening at one end. The capsule 1102 may be configured to encapsulate the flexible PMUT array 1104 and the electronic components 1006. FIG. 11A shows the view of the flexible PMUT array 1104, the electronic components 1106, the inflatable device 1108, and other related components (not shown) prior to being inserted into the capsule 1102. According to aspects of the present disclosure, the other related components may include, but not limited to, battery, flexible printed circuit board, rigid-flexible printed circuit board, or some combinations thereof. The cross sectional view is further described below in association with the discussion of FIG. 11B.

In FIG. 11B, on the left hand side, a side view of the flexible PMUT array 1104, the electronic components 1106, the inflatable device 1108, the coupling material 1110, and other related components after they are being inserted into the capsule 1102 is shown. In the middle, a cross sectional view of the flexible PMUT array 1104, the electronic components 1106, the inflatable device 1108, the coupling material 1110, and other related components after they are being inserted into the capsule 1102 is shown. On the right hand side, an enlarged cross sectional view is shown.

As shown in FIG. 11B, moving from inside to outside in the enlarged cross sectional view, the electronic components 1106 may be placed in the middle of the capsule, which is then sandwiched by the inflatable device 1108; the next layer may be the flexible PMUT array 1104; the next layer may be the coupling material 1110 (also referred to as bonding material); the next layer may be an air gap 1112; and the outer most layer is the capsule 1102.

In FIG. 11C, the inflatable device 1108 may be inflated to a predetermined pressure so that it is configured to push the flexible PMUT array 1104, and the coupling material 1110 against the inner wall of the capsule 1102. On the left hand side, a side view of the flexible PMUT array 1104, the electronic components 1106, the inflatable device 1108, the coupling material 1110, and other related components after they are being pushed against the inner wall of the capsule 1102 is shown. On the right hand side, a cross sectional view of the flexible PMUT array 1104, the electronic components 1106, the inflatable device 1108, the coupling material 1110, and other related components after they are being pushed against the inner wall of the capsule 1102 is shown.

According to aspects of the present disclosure, the air gap 1112 between the coupling material 1110 and the inner wall of the capsule 1102 may be substantially removed by the process of inflating the inflatable device 1108. The coupling material 1110 may then be cured, for example by heat, UV light, or through other means. As a result of the curing process, the flexible PMUT array 1104, the electronic components 1106, and other related components can be firmly held in the capsule 1102.

In FIG. 11D, the inflatable device 1108 may then be deflated. On the left hand side, a side view of the inflatable device 1108 after it is being deflated is shown. On the right hand side, a cross sectional view of the inflatable device 1108 after it is being deflated is shown. FIG. 11E shows the side view and the cross sectional view of the sensor device with the flexible PMUT array 1104, the electronic components 1106, and other related components being attached to the inner wall of the capsule 1102 using the coupling material 1110. After the inflatable device 1108 has been removed, the capsule 1102 may then be sealed.

According to aspects of the present disclosure, the sensor device as formed by using the methods and processes described from FIG. 1A-1B to FIG. 11A-11E may be employed in medical applications. For example, the sensor device may be configured in such a way that it may be swallowed by a patient, or it may be injected or implanted in a patient. In addition, the sensor device may be placed into a stent, catheter or other mechanical means for accessing and monitoring a patient. The sensor device may hermetically sealed and may be made of glass, ceramic, titanium, or other materials that may minimize any reactions after being ingested, injected, or implanted in the body of the patent.

In an exemplary implementation, the sensor device as formed by using the methods and processes described from FIG. 1A-1B to FIG. 11A-11E may be compact and light weight. The physical characteristics of the sensor device may have a height of 10.9 mm, a diameter of 2.6 mm, a weight of 0.2 gram, and a volume of 0.06 cc. The electrical characteristics of the sensor device may have a nominal capacity of 1.5 mAh, a nominal voltage of 3.6V, a maximum recommended continuous discharge current of 1.5 mA, and an operating discharge temperature of 0° C. to 42° C. The sensor device may be Zero-Volt™ enabled, hermetically sealed, and implantable. The sensor device may support biocompatibility and retains over 80% of its original capacity at 500 cycles. It may further have low self-discharge and long calendar life at elevated temperatures. In some other implementations, the capsule may be implemented in different sizes ranging from 11.1 millimeter (mm) to 26.1 mm in length and 4.91 mm to 9.91 mm in diameter.

According to aspects of the present disclosure, a method of forming an array of piezoelectric micromechanical ultrasonic transducers (PMUTs) comprises, for each piezoelectric micromechanical ultrasonic transducer (PMUT) in the array of PMUTs: laminating a first polymer layer configured to support the PMUT, depositing a sacrificial material configured to pattern a cavity of the PMUT, depositing a mechanical layer configured to provide planarization to the PMUT, depositing a first electrode configured to be coupled to a circuit ground plane, depositing a piezoelectric layer configured to separate the first electrode and a second electrode, depositing the second electrode configured to be coupled to a signal, and creating patterns on the first electrode, the piezoelectric material, and the second electrode configured to implement a design of the PMUT. Note that the mechanical layer may include a planarization layer configured to provide chemical mechanical planarization to the PMUT, a mechanical membrane configured to provide stiffness to the PMUT, or some combination thereof.

In some implementations, the method may further include, prior to laminating the first polymer layer, providing a carrier configured to support the PMUT, and providing a release layer configured to adhere first polymer layer of the PMUT to the carrier. The method may yet further include depositing a passivation layer configured to encapsulate the first electrode, the piezoelectric layer and the second electrode, etching contact vias configured to access the first electrode and the second electrode, and depositing pads and/or a redistribution layer configured to route electric signals to the first electrode and the second electrode.

Upon depositing the pads and/or redistribution layer configured to route electric signals to the first electrode and the second electrode, the method may further include forming a cavity configured to adjust a frequency response of the PMUT, and removing the release layer to separate the PMUT from the carrier. In an alternative implementation, the method may include forming a cavity configured to adjust a frequency response of the PMUT, laminating an encapsulation polymer configured to protect the PMUT, forming pattern vias configured to support signal access through the redistribution layer, and removing the release layer to separate the PMUT from the carrier. In another alternative implementation, the method may include laminating an encapsulation polymer configured to protect the PMUT, forming pattern vias configured to support signal access through the redistribution layer, removing the release layer to separate the PMUT from the carrier, drilling a release via in the first polymer layer, and forming a cavity configured to adjust a frequency response of the PMUT by removing the sacrificial material using the release via.

Upon providing a release layer configured to adhere first polymer layer of the PMUT to the carrier, the method may further include laminating a passivation polymer configured to encapsulate the first electrode, the piezoelectric layer and the second electrode, patterning contact vias configured to access the first electrode and the second electrode, and depositing pads and/or a redistribution layer configured to route electric signals to the first electrode and the second electrode. Next, in one exemplary implementation, the method may further include forming a cavity configured to adjust a frequency response of the PMUT, and removing the release layer to separate the PMUT from the carrier. In an alternative exemplary implementation, the method may include forming a cavity configured to adjust a frequency response of the PMUT, laminating an encapsulation polymer configured to protect the PMUT, forming pattern vias configured to support signal access through the redistribution layer, and removing the release layer to separate the PMUT from the carrier. In yet another alternative exemplary implementation, the method may further include laminating an encapsulation polymer configured to protect the PMUT, forming pattern vias configured to support signal access through the redistribution layer, removing the release layer to separate the PMUT from the carrier, drilling a release via in the first polymer layer, and forming a cavity configured to adjust a frequency response of the PMUT by removing the sacrificial material using the release via.

The methodologies described herein may be implemented by various means depending upon applications according to particular examples. For example, such methodologies may be implemented in hardware, firmware, software, or combinations thereof. In a hardware implementation, for example, a processing unit may be implemented within one or more application specific integrated circuits ("ASICs"), digital signal processors ("DSPs"), digital signal processing devices ("DSPDs"), programmable logic devices ("PLDs"), field programmable gate arrays ("FPGAs"), processors, controllers, micro-controllers, microprocessors, electronic devices, other devices units designed to perform the functions described herein, or combinations thereof.

Some portions of the detailed description included herein are presented in terms of algorithms or symbolic representations of operations on binary digital signals stored within a memory of a specific apparatus or special purpose computing device or platform. In the context of this particular specification, the term specific apparatus or the like includes a general purpose computer once it is programmed to perform particular operations pursuant to instructions from program software. Algorithmic descriptions or symbolic representations are examples of techniques used by those of ordinary skill in the signal processing or related arts to convey the substance of their work to others skilled in the art. An algorithm is here, and generally, is considered to be a self-consistent sequence of operations or similar signal processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals, or the like. It should be understood, however, that all of these or similar terms are to be associated with appropriate physical quantities and are merely convenient labels. Unless specifically stated otherwise, as apparent from the discussion herein, it is appreciated that throughout this specification discussions utilizing terms such as "processing," "computing," "calculating," "determining" or the like refer to actions or processes of a specific apparatus, such as a special purpose computer, special purpose computing apparatus or a similar special purpose electronic computing device. In the context of this specification, therefore, a special purpose computer or a similar special purpose electronic computing device is capable of manipulating or transforming signals, typically represented as physical electronic or magnetic quantities within memories, registers, or other information storage devices, transmission devices, or display devices of the special purpose computer or similar special purpose electronic computing device.

Wireless communication techniques described herein may be in connection with various wireless communications networks such as a wireless wide area network ("WWAN"), a wireless local area network ("WLAN"), a wireless personal area network (WPAN), and so on. The term "network" and "system" may be used interchangeably herein. A WWAN may be a Code Division Multiple Access ("CDMA") network, a Time Division Multiple Access ("TDMA") network, a Frequency Division Multiple Access ("FDMA") network, an Orthogonal Frequency Division Multiple Access ("OFDMA") network, a Single-Carrier Frequency Division Multiple Access ("SC-FDMA") network, or any combination of the above networks, and so on. A CDMA network may implement one or more radio access technologies ("RATs") such as cdma2000, Wideband-CDMA ("W-CDMA"), to name just a few radio technologies. Here, cdma2000 may include technologies implemented according to IS-95, IS-2000, and IS-856 standards.

A TDMA network may implement Global System for Mobile Communications ("GSM"), Digital Advanced Mobile Phone System ("D-AMPS"), or some other RAT. GSM and W-CDMA are described in documents from a consortium named "3rd Generation Partnership Project" ("3GPP"). Cdma2000 is described in documents from a consortium named "3rd Generation Partnership Project 2" ("3GPP2"). 3GPP and 3GPP2 documents are publicly available. 4G Long Term Evolution ("LTE") communications networks may also be implemented in accordance with claimed subject matter, in an aspect. A WLAN may comprise an IEEE 802.11x network, and a WPAN may comprise a Bluetooth® network, an IEEE 802.15x, for example. Wireless communication implementations described herein may also be used in connection with any combination of WWAN, WLAN or WPAN.

In another aspect, as previously mentioned, a wireless transmitter or access point may comprise a femtocell, utilized to extend cellular telephone service into a business or home. In such an implementation, one or more mobile devices may communicate with a femtocell via a code division multiple access ("CDMA") cellular communication protocol, for example, and the femtocell may provide the mobile device access to a larger cellular telecommunication network by way of another broadband network such as the Internet.

Techniques described herein may be used with a GPS that includes any one of several GNSS and/or combinations of GNSS. Furthermore, such techniques may be used with positioning systems that utilize terrestrial transmitters acting as "pseudolites", or a combination of satellite vehicles (SVs) and such terrestrial transmitters. Terrestrial transmitters may, for example, include ground-based transmitters that broadcast a PN code or other ranging code (e.g., similar to a GPS or CDMA cellular signal). Such a transmitter may be assigned a unique PN code so as to permit identification by a remote receiver. Terrestrial transmitters may be useful, for example, to augment a GPS in situations where GPS signals from an orbiting SV might be unavailable, such as in tunnels, mines, buildings, urban canyons or other enclosed areas. Another implementation of pseudolites is known as radio-beacons. The term "SV", as used herein, is intended to include terrestrial transmitters acting as pseudolites, equivalents of pseudolites, and possibly others. The terms "GPS signals" and/or "SV signals", as used herein, is intended to include GPS-like signals from terrestrial transmitters, including terrestrial transmitters acting as pseudolites or equivalents of pseudolites.

The terms, "and," and "or" as used herein may include a variety of meanings that will depend at least in part upon the context in which it is used. Typically, "or" if used to associate a list, such as A, B or C, is intended to mean A, B, and C, here used in the inclusive sense, as well as A, B or C, here used in the exclusive sense. Reference throughout this specification to "one example" or "an example" means that a particular feature, structure, or characteristic described in connection with the example is included in at least one example of claimed subject matter. Thus, the appearances of the phrase "in one example" or "an example" in various places throughout this specification are not necessarily all referring to the same example. Furthermore, the particular features, structures, or characteristics may be combined in one or more examples. Examples described herein may include machines, devices, engines, or apparatuses that operate using digital signals. Such signals may comprise electronic signals, optical signals, electromagnetic signals, or any form of energy that provides information between locations.

While there has been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter may also include all aspects falling within the scope of the appended claims, and equivalents thereof.

We claim:

1. A sensor device, comprising:
   a piezoelectric micromechanical ultrasonic transducer (PMUT) array configured to transmit and receive ultrasonic signals, wherein the PMUT array comprises a plurality of PMUTs, and the PMUT array is flexible;
   one or more integrated circuits configured to process the ultrasonic signals;
   a battery configured to provide power to the PMUT array and the one or more integrated circuits;
   a coupling material configured to hold the PMUT array, the one or more integrated circuits, and the battery; and
   a capsule configured to seal the PMUT array, the one or more integrated circuits, the battery and the coupling material within the capsule.

2. The sensor device of claim 1, wherein each PMUT in the PMUT array comprises:
   a first polymer layer configured to support the PMUT;
   a cavity configured to control a frequency response of the PMUT;
   a mechanical layer configured to provide planarization to the PMUT;
   a first electrode configured to be coupled to a circuit ground plane;
   a second electrode configured to be coupled to a signal; and
   a piezoelectric layer configured to separate the first electrode and the second electrode.

3. The sensor device of claim 2, wherein the cavity is oriented to face outwards from the capsule, wherein the cavity is configured to control the PMUT to operate in a first range of frequency response.

4. The sensor device of claim 2, wherein the cavity is oriented to face inwards from the capsule, wherein the cavity is configured to control the PMUT to operate in a second range of frequency response.

5. The sensor device of claim 2, wherein cavity is enclosed in one or more substrates of the PMUT, wherein the cavity encapsulates a gaseous medium and is configured to control the PMUT to operate in a third range of frequency response.

6. The sensor device of claim 1, further comprises:
   at least one of a flexible printed circuit board or a rigid-flex printed circuit board configured to attach to the one or more integrated circuits; wherein the at least one of the flexible printed circuit board or the rigid-flex printed circuit board is coupled to the PMUT array.

7. The sensor device of claim 6, wherein the one or more integrated circuits are implemented on a thin silicon die, and wherein the thin silicon die is coupled to the PMUT array.

8. The sensor device of claim 6, wherein the PMUT array, the one or more integrated circuits, the battery and the coupling material are inserted into the capsule by an inflatable device.

9. The sensor device of claim 8, wherein the inflatable device has a cylindrical shape, and wherein the PMUT array, the one or more integrated circuits, the battery and the coupling material are wrapped around the inflatable device.

10. The sensor device of claim 8, wherein the inflatable device has a U-shape; wherein the PMUT array and the coupling material are wrapped around the inflatable device, and the one or more integrated circuits and the battery are sandwiched by the inflatable device.

11. The sensor device of claim 8, wherein the PMUT array, the one or more integrated circuits, the battery and the coupling material are pushed against the inner wall of the capsule by inflating the inflatable device.

12. The sensor device of claim 11, wherein the coupling material is cured by heat or UV light while the coupling material is being pushed against the inner wall of the capsule by the inflatable device.

13. The sensor device of claim 12, wherein the inflatable device is deflated and removed from the capsule after the coupling material is cured, attaching the PMUT array, the one or more integrated circuits, and the battery to the inner wall of the capsule.

14. The sensor device of claim 13, wherein the capsule is sealed after the inflatable device is removed.

15. The sensor device of claim 14, wherein the capsule is made of glass, ceramic, titanium, or some combination thereof.

16. A method of manufacturing a sensor device, comprising:
providing a piezoelectric micromechanical ultrasonic transducer (PMUT) array configured to transmit and receive ultrasonic signals, wherein the PMUT array comprises a plurality of PMUTs, and the PMUT array is flexible;
providing one or more integrated circuits configured to process the ultrasonic signals;
providing a battery configured to provide power to the PMUT array and the one or more integrated circuits;
providing a coupling material configured to hold the PMUT array, the one or more integrated circuits, and the battery; and
providing a capsule configured to seal the PMUT array, the one or more integrated circuits, the battery and the coupling material within the capsule.

17. The method of claim 16, wherein each PMUT in the PMUT array comprises:
a first polymer layer configured to support the PMUT;
a cavity configured to control a frequency response of the PMUT;
a mechanical layer configured to provide planarization to the PMUT;
a first electrode configured to be coupled to a circuit ground plane;
a second electrode configured to be coupled to a signal; and
a piezoelectric layer configured to separate the first electrode and the second electrode.

18. The method of claim 17 further comprising:
orienting the cavity to face outwards from the capsule, wherein the cavity is configured to control the PMUT to operate in a first range of frequency response.

19. The method of claim 17 further comprising:
orienting the cavity to face inwards from the capsule, wherein the cavity is configured to control the PMUT to operate in a second range of frequency response.

20. The method of claim 17 further comprising:
enclosing the cavity in one or more substrates of the PMUT, wherein the cavity encapsulates a gaseous medium and is configured to control the PMUT to operate in a third range of frequency response.

21. The method of claim 17, further comprising:
attaching the one or more integrated circuits to at least one of a flexible printed circuit board or a rigid-flex printed circuit board; and
attaching the at least one of the flexible printed circuit board or the rigid-flex printed circuit board to the PMUT array.

22. The method of claim 21, wherein the one or more integrated circuits are implemented on a thin silicon die, and wherein the thin silicon die is coupled to the PMUT array.

23. The method of claim 21 further comprising:
inserting the PMUT array, the one or more integrated circuits, the battery and the coupling material into the capsule by an inflatable device.

24. The method of claim 23, wherein the inflatable device has a cylindrical shape, and wherein the PMUT array, the one or more integrated circuits, the battery and the coupling material are wrapped around the inflatable device.

25. The method of claim 23, wherein the inflatable device has a U-shape; wherein the PMUT array and the coupling material are wrapped around the inflatable device, and the one or more integrated circuits and the battery are sandwiched by the inflatable device.

26. The method of claim 23 further comprising:
inflating the inflatable device to push the PMUT array, the one or more integrated circuits, the battery and the coupling material against the inner wall of the capsule.

27. The method of claim 26 further comprising:
curing the coupling material by heat or UV light while the coupling material is being pushed against the inner wall of the capsule by the inflatable device.

28. The method of claim 27,
deflating the inflatable device after the coupling material is cured, attaching the PMUT array, the one or more integrated circuits, and the battery to the inner wall of the capsule; and
removing the inflatable device from the capsule.

29. The method of claim 28 further comprising:
sealing the capsule after the inflatable device is removed.

30. The method of claim 29, wherein the capsule is made of glass, ceramic, titanium, or some combination thereof.

* * * * *